(12) United States Patent
Fancher

(10) Patent No.: US 11,576,563 B2
(45) Date of Patent: Feb. 14, 2023

(54) ENDOSCOPE WITH SEPARABLE, DISPOSABLE SHAFT

(71) Applicant: AdaptivEndo LLC, Louisville, KY (US)

(72) Inventor: Hershel E. Fancher, Georgetown, IN (US)

(73) Assignee: AdaptivEndo LLC, Louisville, KY (US)

(*) Notice: Subject to any disclaimer, the term of this patent is extended or adjusted under 35 U.S.C. 154(b) by 369 days.

(21) Appl. No.: 16/421,523

(22) Filed: May 24, 2019

(65) Prior Publication Data

US 2019/0313881 A1    Oct. 17, 2019

Related U.S. Application Data

(63) Continuation of application No. PCT/US2017/063413, filed on Nov. 28, 2017.
(Continued)

(51) Int. Cl.
*A61B 1/008* (2006.01)
*A61B 1/00* (2006.01)
*A61B 1/005* (2006.01)

(52) U.S. Cl.
CPC .......... *A61B 1/008* (2013.01); *A61B 1/00009* (2013.01); *A61B 1/00016* (2013.01);
(Continued)

(58) Field of Classification Search
CPC . A61B 1/008; A61B 1/00009; A61B 1/00016; A61B 1/00103; A61B 1/00128; A61B 1/0052; A61B 1/0057
See application file for complete search history.

(56) References Cited

U.S. PATENT DOCUMENTS 4,253,448 A    3/1981 Terada
4,261,345 A    4/1981 Yamaguchi
(Continued)

FOREIGN PATENT DOCUMENTS

CH    713337    12/2016
CN    102740758 A    10/2012
(Continued)

OTHER PUBLICATIONS

PCT Search Report and Written Opinion for PCT/US17/63413, dated Jan. 30, 2018.
(Continued)

*Primary Examiner* — John P Leubecker
*Assistant Examiner* — Jae Woo
(74) *Attorney, Agent, or Firm* — Woodard, Emhardt, Henry, Reeves & Wagner, LLP

(57) ABSTRACT

Endoscopes comprising a reusable hand-piece and separable disposable shaft assembly are illustrated and described. The reusable hand-piece includes a housing having an articulation control mounted thereto and an electronics module mounted thereto. The articulation control includes control knobs and concentric drive shafts for articulation. The electronics module includes a battery, a control board, and an optical and/or electrical connector. The separable disposable shaft comprises a housing having an articulation wire actuating assembly mounted thereto and an optical and/or electrical connector mounted thereto. When the housing of the hand-piece and the housing of the separable disposable shaft assembly are joined together, the articulation control engages the articulation wire actuating assembly and the optical and/or electrical connector of the reusable hand-piece engages the optical and/or electrical connector of the disposable shaft assembly.

13 Claims, 24 Drawing Sheets

Related U.S. Application Data

(60) Provisional application No. 62/426,886, filed on Nov. 28, 2016.

(52) U.S. Cl.
CPC .......... *A61B 1/0052* (2013.01); *A61B 1/0057* (2013.01); *A61B 1/00103* (2013.01); *A61B 1/00128* (2013.01)

(56) References Cited

U.S. PATENT DOCUMENTS

| | | | |
|---|---|---|---|
| 4,700,693 A | 10/1987 | Lia et al. | |
| 4,726,119 A | 2/1988 | Lee | |
| 4,790,294 A | 12/1988 | Allred, III et al. | |
| 4,796,607 A | 1/1989 | Allred, III et al. | |
| 4,919,621 A | 4/1990 | Arns | |
| 4,947,245 A * | 8/1990 | Ogawa | A61B 1/00101 348/66 |
| 5,014,685 A | 5/1991 | Takahashi | |
| 5,479,930 A * | 1/1996 | Gruner | A61B 1/0052 600/146 |
| 5,549,542 A | 8/1996 | Kovalcheck | |
| 5,792,165 A | 8/1998 | Klieman et al. | |
| 5,846,221 A * | 12/1998 | Snoke | A61B 1/0052 604/500 |
| 6,482,149 B1 | 11/2002 | Torii | |
| 6,610,007 B2 | 8/2003 | Belson et al. | |
| 6,641,528 B2 | 11/2003 | Torii | |
| D486,910 S | 2/2004 | Hayamizu et al. | |
| 6,702,737 B2 | 4/2004 | Hino | |
| 6,811,532 B2 | 11/2004 | Ogura et al. | |
| 6,905,461 B2 | 6/2005 | Hino | |
| 7,169,105 B2 | 1/2007 | Iwasaka et al. | |
| 7,250,027 B2 | 7/2007 | Barry | |
| 7,326,176 B2 | 2/2008 | Machiya et al. | |
| 7,410,483 B2 | 8/2008 | Danitz et al. | |
| 7,413,543 B2 | 8/2008 | Banik et al. | |
| 7,578,786 B2 | 8/2009 | Boulais et al. | |
| 7,588,536 B2 * | 9/2009 | Peszynski | A61B 1/0052 600/144 |
| 7,678,117 B2 | 3/2010 | Hinman et al. | |
| 7,708,182 B2 | 5/2010 | Viola | |
| 7,905,828 B2 * | 3/2011 | Brock | A61B 34/30 600/114 |
| 7,909,220 B2 | 3/2011 | Viola | |
| 8,016,749 B2 | 9/2011 | Clerc et al. | |
| 8,029,531 B2 * | 10/2011 | Lee | A61B 1/0052 606/205 |
| 8,246,575 B2 | 8/2012 | Viola | |
| 8,308,044 B2 | 11/2012 | Viola | |
| 8,323,297 B2 | 12/2012 | Hinman et al. | |
| 8,348,834 B2 | 1/2013 | Bakos | |
| 8,377,059 B2 * | 2/2013 | Deville | A61B 18/1445 606/45 |
| 8,419,623 B2 | 4/2013 | Garcia et al. | |
| 8,465,420 B2 | 6/2013 | Ostrovsky et al. | |
| 8,475,366 B2 | 7/2013 | Boulais et al. | |
| 8,517,924 B2 | 8/2013 | Banik et al. | |
| 8,517,926 B2 | 8/2013 | Uchimura | |
| 8,529,554 B2 | 9/2013 | Murakami et al. | |
| 8,602,967 B2 | 12/2013 | Robertson | |
| 8,608,648 B2 | 12/2013 | Banik et al. | |
| 8,608,649 B2 | 12/2013 | McWeeney et al. | |
| 8,657,178 B2 * | 2/2014 | Hueil | A61B 17/068 227/180.1 |
| 8,690,760 B2 | 4/2014 | Robertson et al. | |
| 8,777,842 B2 | 7/2014 | Endo et al. | |
| 8,820,605 B2 * | 9/2014 | Shelton, IV | A61B 17/07207 227/175.1 |
| 8,827,899 B2 | 9/2014 | Farr et al. | |
| 8,827,949 B2 | 9/2014 | Boulais | |
| 8,858,425 B2 | 10/2014 | Farr et al. | |
| 8,876,703 B2 | 11/2014 | Omoto | |
| 8,876,705 B2 | 11/2014 | Mathieu et al. | |
| 8,888,682 B2 | 11/2014 | Kawasaki et al. | |
| 8,894,566 B2 | 11/2014 | Ikuma et al. | |
| 8,915,841 B2 | 12/2014 | Naito | |
| 8,928,746 B1 | 1/2015 | Stevrin et al. | |
| 8,957,952 B2 | 2/2015 | Tashiro et al. | |
| 8,961,402 B2 | 2/2015 | Okamoto | |
| D724,209 S | 3/2015 | Sun | |
| 8,979,741 B2 | 3/2015 | Igarashi et al. | |
| 8,998,800 B2 | 4/2015 | Masaki | |
| 9,002,285 B2 | 4/2015 | Hasegawa et al. | |
| 9,028,397 B2 | 5/2015 | Naito | |
| 9,030,544 B2 | 5/2015 | Tashiro et al. | |
| 9,033,870 B2 | 5/2015 | Farr et al. | |
| 9,055,864 B2 | 6/2015 | Le et al. | |
| 9,078,616 B2 | 7/2015 | Uchiyama et al. | |
| 9,085,085 B2 | 7/2015 | Danitz et al. | |
| 9,089,259 B2 | 7/2015 | Takeuchi | |
| 9,095,253 B2 | 8/2015 | Hinman et al. | |
| 9,119,527 B2 | 9/2015 | Endo et al. | |
| 9,149,174 B2 | 10/2015 | Machida et al. | |
| 9,155,456 B2 | 10/2015 | Koshikawa | |
| 9,155,865 B2 | 10/2015 | Golden et al. | |
| 9,186,041 B2 | 11/2015 | Kasumi et al. | |
| 9,198,714 B2 | 12/2015 | Worrell et al. | |
| 9,204,781 B2 | 12/2015 | Taniguchi | |
| 9,204,783 B2 | 12/2015 | Kappel et al. | |
| 9,211,057 B2 | 12/2015 | Takei | |
| 9,215,970 B2 | 12/2015 | Boutillette et al. | |
| 9,314,147 B2 | 4/2016 | Levy et al. | |
| 9,339,173 B2 | 5/2016 | McWeeney et al. | |
| 9,345,503 B2 | 5/2016 | Ishida et al. | |
| 9,370,868 B2 | 6/2016 | Danitz et al. | |
| 9,434,077 B2 | 9/2016 | Danitz et al. | |
| 9,700,334 B2 | 7/2017 | Hinman et al. | |
| 9,895,185 B2 | 2/2018 | Hoey et al. | |
| 10,939,809 B2 | 3/2021 | Bock et al. | |
| 2002/0032370 A1 | 3/2002 | Kamata et al. | |
| 2003/0004460 A1 * | 1/2003 | Bedell | A61M 25/0136 604/95.04 |
| 2004/0015054 A1 | 1/2004 | Hino | |
| 2004/0199052 A1 | 10/2004 | Banik et al. | |
| 2004/0242966 A1 | 12/2004 | Barry et al. | |
| 2005/0006433 A1 * | 1/2005 | Milliman | A61B 17/1114 227/176.1 |
| 2005/0272975 A1 * | 12/2005 | McWeeney | A61B 1/008 600/113 |
| 2006/0069307 A1 | 3/2006 | Boulais | |
| 2006/0149127 A1 * | 7/2006 | Seddiqui | A61B 1/0052 600/104 |
| 2006/0235304 A1 | 10/2006 | Harhen et al. | |
| 2006/0287576 A1 | 12/2006 | Tsuji et al. | |
| 2007/0043261 A1 | 2/2007 | Watanabe et al. | |
| 2008/0108869 A1 * | 5/2008 | Sanders | A61B 1/00103 600/109 |
| 2008/0125628 A1 * | 5/2008 | Ueno | A61B 1/0016 600/130 |
| 2008/0207028 A1 | 8/2008 | Schutz | |
| 2008/0262300 A1 * | 10/2008 | Ewers | A61B 1/0051 600/114 |
| 2009/0126862 A1 | 5/2009 | Leeflang et al. | |
| 2009/0227841 A1 | 9/2009 | Miyako et al. | |
| 2010/0048999 A1 | 2/2010 | Boulais et al. | |
| 2010/0106147 A1 * | 4/2010 | Boitor | A61B 18/22 606/16 |
| 2010/0191053 A1 * | 7/2010 | Garcia | A61B 1/00105 600/109 |
| 2010/0223697 A1 | 9/2010 | Moeck | |
| 2010/0249817 A1 * | 9/2010 | Mark | A61B 17/32002 606/170 |
| 2011/0021871 A1 * | 1/2011 | Berkelaar | A61B 1/00105 600/104 |
| 2011/0245602 A1 | 10/2011 | Brannon | |
| 2011/0263938 A1 | 10/2011 | Levy | |
| 2012/0016191 A1 | 1/2012 | Ito et al. | |
| 2012/0065469 A1 | 3/2012 | Allyn et al. | |
| 2012/0100729 A1 * | 4/2012 | Edidin | A61B 1/0057 439/38 |
| 2012/0220832 A1 | 8/2012 | Nakade et al. | |

(56) References Cited

U.S. PATENT DOCUMENTS

| | | |
|---|---|---|
| 2012/0296167 A1 | 11/2012 | Chen et al. |
| 2012/0302835 A1 | 11/2012 | Mathieu et al. |
| 2013/0030428 A1* | 1/2013 | Worrell ............ A61B 17/07207 606/33 |
| 2013/0158379 A1* | 6/2013 | Selkee .................. A61B 5/283 600/373 |
| 2013/0172813 A1* | 7/2013 | Caples .............. A61M 25/0136 604/95.04 |
| 2013/0261396 A1 | 10/2013 | Boulais et al. |
| 2014/0111634 A1* | 4/2014 | Mueckl .............. G02B 23/2476 348/82 |
| 2014/0221749 A1* | 8/2014 | Grant ................ A61B 1/00183 600/112 |
| 2014/0257037 A1 | 9/2014 | Hino |
| 2014/0275763 A1* | 9/2014 | King .................. A61B 1/00103 600/103 |
| 2014/0343489 A1* | 11/2014 | Lang .................... A61B 1/0052 604/95.04 |
| 2015/0359416 A1 | 12/2015 | Simchony et al. |
| 2015/0366436 A1* | 12/2015 | Iuel ...................... A61B 1/0051 600/149 |
| 2016/0000300 A1* | 1/2016 | Williams ........... A61B 1/00039 600/109 |
| 2016/0058268 A1* | 3/2016 | Salman ................ A61B 1/0055 600/149 |
| 2016/0073856 A1* | 3/2016 | Saito .................... A61B 1/0052 600/149 |
| 2016/0199058 A1 | 7/2016 | Chlysta |
| 2016/0262595 A1 | 9/2016 | Kakehashi |
| 2016/0287779 A1 | 10/2016 | Orczy-Timko et al. |
| 2017/0231475 A1 | 8/2017 | McWeeney et al. |
| 2017/0333606 A1 | 11/2017 | Manandhar et al. |
| 2018/0028048 A1 | 2/2018 | Simmons et al. |
| 2018/0200416 A1* | 7/2018 | Oza ...................... A61B 1/2733 |
| 2018/0206710 A1 | 7/2018 | Krivopisk et al. |
| 2018/0214015 A1 | 8/2018 | Calabrese et al. |
| 2018/0218233 A1 | 8/2018 | Yamanashi et al. |
| 2018/0228355 A1 | 8/2018 | Daidoji et al. |
| 2018/0234646 A1 | 8/2018 | Kobayashi |
| 2018/0242817 A1 | 8/2018 | Imaizumi et al. |
| 2018/0242832 A1 | 8/2018 | Morimoto et al. |
| 2018/0242893 A1 | 8/2018 | Saito |
| 2018/0242958 A1 | 8/2018 | Dayton et al. |
| 2018/0296063 A1 | 10/2018 | Motoki |
| 2018/0296068 A1 | 10/2018 | Matthison-Hansen et al. |
| 2018/0296069 A1 | 10/2018 | Matthison-Hansen |
| 2018/0296077 A1 | 10/2018 | Suzuki et al. |
| 2018/0296186 A1 | 10/2018 | Harks et al. |
| 2018/0296281 A1 | 10/2018 | Yeung et al. |
| 2018/0296285 A1 | 10/2018 | Simi et al. |
| 2018/0302586 A1 | 10/2018 | Motoki |
| 2018/0303315 A1 | 10/2018 | Matthison-Hansen |
| 2018/0303316 A1 | 10/2018 | Matthison-Hansen |
| 2018/0303317 A1 | 10/2018 | Matthison-Hansen |
| 2018/0303324 A1 | 10/2018 | Hashiba et al. |
| 2018/0303325 A1 | 10/2018 | Fujimori |
| 2018/0303472 A1 | 10/2018 | Matthison-Hansen et al. |
| 2018/0307023 A1 | 10/2018 | Jess et al. |
| 2018/0309908 A1 | 10/2018 | Matthison-Hansen et al. |
| 2018/0333040 A1 | 11/2018 | Harada et al. |
| 2018/0333043 A1 | 11/2018 | Terliuc et al. |
| 2018/0338152 A1 | 11/2018 | Yamauchi |
| 2018/0341110 A1 | 11/2018 | Hirata et al. |
| 2018/0342079 A1 | 11/2018 | Yaguchi |
| 2018/0344129 A1 | 12/2018 | Shiraishi |
| 2018/0344131 A1 | 12/2018 | Takahira et al. |
| 2018/0344136 A1 | 12/2018 | Kikuchi |
| 2018/0344140 A1 | 12/2018 | Aizenfeld |
| 2018/0346150 A1 | 12/2018 | Remond et al. |
| 2018/0360296 A1 | 12/2018 | Sato et al. |
| 2018/0368657 A1 | 12/2018 | Yamamoto |
| 2018/0368658 A1 | 12/2018 | Yamamoto |
| 2018/0368664 A1 | 12/2018 | Nagda et al. |
| 2018/0368668 A1 | 12/2018 | Ida |
| 2018/0368670 A1 | 12/2018 | Watanabe et al. |
| 2018/0368671 A1 | 12/2018 | Nakayama |
| 2018/0376119 A1 | 12/2018 | Iwane |
| 2019/0000303 A1 | 1/2019 | Suzuki et al. |
| 2019/0005641 A1 | 1/2019 | Yamamoto |
| 2019/0008359 A1 | 1/2019 | Ma et al. |
| 2019/0008362 A1 | 1/2019 | Kamon |
| 2019/0008365 A1 | 1/2019 | Kirma et al. |
| 2019/0008372 A1 | 1/2019 | Tanaka et al. |
| 2019/0008374 A1 | 1/2019 | Yamamoto |
| 2019/0013444 A1 | 1/2019 | Morimoto et al. |
| 2019/0014971 A1 | 1/2019 | Petersen et al. |
| 2019/0014972 A1 | 1/2019 | Hatano et al. |
| 2019/0014974 A1 | 1/2019 | Hatano et al. |
| 2019/0015172 A1 | 1/2019 | Yamaya |
| 2019/0021576 A1 | 1/2019 | Karl |
| 2019/0021579 A1 | 1/2019 | Kamon |
| 2019/0029494 A1 | 1/2019 | Araki |
| 2019/0029500 A1 | 1/2019 | McCaffrey et al. |
| 2019/0029503 A1 | 1/2019 | Hanai et al. |
| 2019/0029614 A1 | 1/2019 | Choi |
| 2019/0034509 A1 | 1/2019 | Ding et al. |
| 2019/0038111 A1 | 2/2019 | Endo |
| 2019/0038119 A1 | 2/2019 | Morimoto et al. |
| 2019/0038121 A1 | 2/2019 | Nakamura |
| 2019/0041627 A1 | 2/2019 | Kobayashi |
| 2019/0043215 A1 | 2/2019 | Ito et al. |
| 2019/0046009 A1 | 2/2019 | Wood et al. |
| 2019/0046016 A1 | 2/2019 | Rajarathnam et al. |
| 2019/0046020 A1 | 2/2019 | Shiraki |
| 2019/0046022 A1 | 2/2019 | Matsui et al. |
| 2019/0051039 A1 | 2/2019 | Tsuru et al. |
| 2019/0053688 A1 | 2/2019 | Yamagata |
| 2019/0053690 A1 | 2/2019 | Suzuki et al. |
| 2019/0053861 A1 | 2/2019 | Lwin et al. |
| 2019/0059699 A1 | 2/2019 | Ting |
| 2019/0059700 A1 | 2/2019 | Matsuda |
| 2019/0059701 A1 | 2/2019 | Igarashi |
| 2019/0059702 A1 | 2/2019 | Hosogoe |
| 2019/0059706 A1 | 2/2019 | Lin |
| 2019/0059707 A1 | 2/2019 | Watanabe |
| 2019/0059709 A1 | 2/2019 | Ting |
| 2019/0059712 A1 | 2/2019 | Fujiwara |
| 2019/0066278 A1 | 2/2019 | Suga |
| 2019/0068864 A1 | 2/2019 | Ohashi et al. |
| 2019/0069766 A1 | 3/2019 | Mizukura et al. |
| 2019/0073769 A1 | 3/2019 | Watanabe |
| 2019/0074399 A1 | 3/2019 | Masuda |
| 2019/0079280 A1 | 3/2019 | Yoshida et al. |
| 2019/0080454 A1 | 3/2019 | Hameed et al. |
| 2019/0082094 A1 | 3/2019 | Endo |
| 2019/0082929 A1 | 3/2019 | Watanabe |
| 2019/0082930 A1 | 3/2019 | Shimomura |
| 2019/0082934 A1 | 3/2019 | Matsunaga |
| 2019/0082936 A1 | 3/2019 | Yamazaki |
| 2019/0082941 A1 | 3/2019 | Ubayama et al. |
| 2019/0082943 A1 | 3/2019 | Mitsunaga |
| 2019/0087970 A1 | 3/2019 | Gardyne et al. |
| 2019/0089875 A1 | 3/2019 | Fan |
| 2019/0089920 A1 | 3/2019 | Nakamura |
| 2019/0090720 A1 | 3/2019 | Maeda |
| 2019/0090723 A1 | 3/2019 | Tanaka et al. |
| 2019/0090729 A1 | 3/2019 | Sugiura et al. |
| 2019/0090778 A1 | 3/2019 | Ikeda et al. |
| 2019/0096037 A1 | 3/2019 | Fukazawa et al. |
| 2019/0098272 A1 | 3/2019 | Takenaga et al. |
| 2019/0099061 A1 | 4/2019 | Isobe |
| 2019/0099063 A1 | 4/2019 | Ono |
| 2019/0104922 A1 | 4/2019 | Kasumi |
| 2019/0104923 A1 | 4/2019 | Ostrovsky et al. |
| 2019/0110661 A1 | 4/2019 | Stogner et al. |
| 2019/0110668 A1 | 4/2019 | Weitzner |
| 2019/0110673 A1 | 4/2019 | Ito et al. |
| 2019/0113738 A1 | 4/2019 | Yamamoto |
| 2019/0117041 A1 | 4/2019 | Tanaka et al. |
| 2019/0117045 A1 | 4/2019 | Hosogoe |
| 2019/0117046 A1 | 4/2019 | Briggs |
| 2019/0117055 A1 | 4/2019 | Ito et al. |
| 2019/0117056 A1 | 4/2019 | Sidar et al. |

(56) References Cited

U.S. PATENT DOCUMENTS

| | | |
|---|---|---|
| 2019/0121118 A1 | 4/2019 | Kirma et al. |
| 2019/0125167 A1 | 5/2019 | Taniguchi |
| 2019/0125170 A1 | 5/2019 | Yahagi et al. |
| 2019/0125172 A1 | 5/2019 | Okazaki et al. |
| 2019/0125174 A1 | 5/2019 | Makino |
| 2019/0125400 A1 | 5/2019 | Ibrahim et al. |
| 2019/0133418 A1 | 5/2019 | Furuhata |
| 2019/0133419 A1 | 5/2019 | Hatano et al. |
| 2019/0133420 A1 | 5/2019 | Cornhill et al. |
| 2019/0133422 A1 | 5/2019 | Nakamura |
| 2019/0133425 A1 | 5/2019 | Taniguchi et al. |
| 2019/0133426 A1 | 5/2019 | Matsui et al. |
| 2019/0136070 A1 | 5/2019 | Aizenberg et al. |
| 2019/0142240 A1 | 5/2019 | Hayashi |
| 2019/0142242 A1 | 5/2019 | Yamaya |
| 2019/0142245 A1 | 5/2019 | Hirono |
| 2019/0142250 A1 | 5/2019 | Maas et al. |
| 2019/0142255 A1 | 5/2019 | Kohno et al. |
| 2019/0142523 A1 | 5/2019 | Govrin |
| 2019/0148441 A1 | 5/2019 | Liu |
| 2019/0150707 A1 | 5/2019 | Matsui |
| 2019/0150709 A1 | 5/2019 | Akui |
| 2019/0150710 A1 | 5/2019 | Nakazato |
| 2019/0150711 A1 | 5/2019 | Chiu et al. |
| 2019/0150714 A1 | 5/2019 | Onishi et al. |
| 2019/0150722 A1 | 5/2019 | Yamaya |
| 2019/0159659 A1 | 5/2019 | Wakasone et al. |
| 2019/0159661 A1 | 5/2019 | Itkowitz et al. |
| 2019/0167069 A1 | 6/2019 | Levy et al. |
| 2019/0167084 A1 | 6/2019 | Nakagawa |
| 2019/0167824 A1 | 6/2019 | Rhodes et al. |
| 2019/0174992 A1 | 6/2019 | Fujii |
| 2019/0174993 A1 | 6/2019 | Fujitani et al. |
| 2019/0174995 A1 | 6/2019 | Fukushima et al. |
| 2019/0174997 A1 | 6/2019 | Yamakawa |
| 2019/0174998 A1 | 6/2019 | Bawaadam et al. |
| 2019/0174999 A1 | 6/2019 | Wake |
| 2019/0175001 A1 | 6/2019 | Sekiguchi |
| 2019/0175002 A1 | 6/2019 | Igarashi et al. |
| 2019/0175003 A1 | 6/2019 | Yoshida et al. |
| 2019/0175004 A1 | 6/2019 | Suyama et al. |
| 2019/0175007 A1 | 6/2019 | Sorensen et al. |
| 2019/0175288 A1 | 6/2019 | Herrell et al. |
| 2019/0175296 A1 | 6/2019 | Tate et al. |
| 2019/0175775 A1 | 6/2019 | Fryer et al. |
| 2019/0175938 A1 | 6/2019 | Rezaie et al. |
| 2019/0183315 A1 | 6/2019 | Endo |
| 2019/0183319 A1 | 6/2019 | Aoyama |
| 2019/0192048 A1 | 6/2019 | Makino et al. |
| 2019/0200843 A1 | 7/2019 | Lai et al. |
| 2019/0200847 A1 | 7/2019 | Uchida |
| 2019/0201569 A1 | 7/2019 | Rhodes |
| 2019/0204069 A1 | 7/2019 | Tatsuta et al. |
| 2019/0206053 A1 | 7/2019 | Ichiki |
| 2019/0208984 A1 | 7/2019 | Machiya et al. |
| 2019/0208985 A1 | 7/2019 | Fukuda et al. |
| 2019/0208988 A1 | 7/2019 | Takatsuji et al. |
| 2019/0208991 A1 | 7/2019 | Park |
| 2019/0208992 A1 | 7/2019 | Yamaya |
| 2019/0208993 A1 | 7/2019 | Toriyama et al. |
| 2019/0208997 A1 | 7/2019 | Rout et al. |
| 2019/0208999 A1 | 7/2019 | Konwitz et al. |
| 2019/0209000 A1 | 7/2019 | Treado et al. |
| 2019/0209015 A1 | 7/2019 | Liang et al. |
| 2019/0209124 A1 | 7/2019 | Taniguchi |
| 2019/0209145 A1 | 7/2019 | Herzlinger et al. |
| 2019/0209160 A1 | 7/2019 | Mitelberg et al. |
| 2019/0216292 A1 | 7/2019 | Nakai |
| 2019/0216295 A1 | 7/2019 | Hatano et al. |
| 2019/0216298 A1 | 7/2019 | Lund et al. |
| 2019/0216299 A1 | 7/2019 | Hayakawa |
| 2019/0216303 A1 | 7/2019 | Simmons |
| 2019/0216325 A1 | 7/2019 | Ouyang |
| 2019/0217062 A1 | 7/2019 | Kato |
| 2019/0218394 A1 | 7/2019 | Nagata et al. |
| 2019/0223691 A1 | 7/2019 | Takatsuji |
| 2019/0223692 A1 | 7/2019 | Nakagawa |
| 2019/0223695 A1 | 7/2019 | Hosogoe et al. |
| 2019/0223696 A1 | 7/2019 | Hosogoe et al. |
| 2019/0223697 A1 | 7/2019 | Hosogoe et al. |
| 2019/0223698 A1 | 7/2019 | Hosogoe et al. |
| 2019/0223701 A1 | 7/2019 | Maurice |
| 2019/0223702 A1 | 7/2019 | Kennedy, II et al. |
| 2019/0223760 A1 | 7/2019 | Averbuch et al. |
| 2019/0231173 A1 | 8/2019 | Hosogoe |
| 2019/0231179 A1 | 8/2019 | Hansen et al. |
| 2019/0231181 A1 | 8/2019 | Levy et al. |
| 2019/0238831 A1 | 8/2019 | Kujuuro et al. |
| 2019/0246874 A1 | 8/2019 | Kamon |
| 2019/0246875 A1 | 8/2019 | Mizoguchi et al. |
| 2019/0246877 A1 | 8/2019 | Mitsuya et al. |
| 2019/0246878 A1 | 8/2019 | Bodner |
| 2019/0246880 A1 | 8/2019 | Wu et al. |
| 2019/0246881 A1 | 8/2019 | Aull |
| 2019/0246886 A1 | 8/2019 | Harada et al. |
| 2019/0254501 A1 | 8/2019 | Kojima et al. |
| 2019/0254504 A1 | 8/2019 | Ide |
| 2019/0254508 A1 | 8/2019 | Levin et al. |
| 2019/0254509 A1 | 8/2019 | Aoyama et al. |
| 2019/0254510 A1 | 8/2019 | Onobori |
| 2019/0254563 A1 | 8/2019 | Nakamitsu et al. |
| 2019/0261830 A1 | 8/2019 | Banik et al. |
| 2019/0261832 A1 | 8/2019 | Suzuki et al. |
| 2019/0261835 A1 | 8/2019 | Ostrovsky et al. |
| 2019/0261836 A1 | 8/2019 | Ouyang et al. |
| 2019/0269299 A1 | 9/2019 | Takahashi |
| 2019/0269300 A1 | 9/2019 | Matsui et al. |
| 2019/0269304 A1 | 9/2019 | Blanquart |
| 2019/0269308 A1 | 9/2019 | Miyake et al. |
| 2019/0269478 A1 | 9/2019 | Nakadate et al. |
| 2019/0274517 A1 | 9/2019 | Hatakeyama |
| 2019/0274591 A1 | 9/2019 | Yokota |
| 2019/0282070 A1 | 9/2019 | Vilhelmsen et al. |
| 2019/0282071 A1 | 9/2019 | Ouyang et al. |
| 2019/0282135 A1 | 9/2019 | Ito et al. |
| 2019/0285868 A1 | 9/2019 | Haraguchi et al. |
| 2019/0289179 A1 | 9/2019 | Mitamura |
| 2019/0290108 A1 | 9/2019 | Nakamitsu et al. |
| 2019/0297276 A1 | 9/2019 | Sachdev et al. |
| 2019/0298155 A1 | 10/2019 | Huang et al. |
| 2019/0298156 A1 | 10/2019 | Yamaya |
| 2019/0298570 A1 | 10/2019 | Clement et al. |
| 2019/0307317 A1 | 10/2019 | Matsubara et al. |
| 2019/0313886 A1 | 10/2019 | Hatano et al. |
| 2019/0320880 A1 | 10/2019 | Takahira |
| 2019/0320882 A1 | 10/2019 | Chen et al. |
| 2019/0328212 A1 | 10/2019 | Nakaji et al. |
| 2019/0328214 A1 | 10/2019 | Do |
| 2019/0328215 A1 | 10/2019 | Kolberg |
| 2019/0328216 A1 | 10/2019 | Beyer et al. |
| 2019/0328220 A1 | 10/2019 | Preub |
| 2019/0335978 A1 | 11/2019 | Chiba |
| 2019/0335979 A1 | 11/2019 | Moriya |
| 2019/0343372 A1 | 11/2019 | Cornhill et al. |
| 2019/0343525 A1 | 11/2019 | Shelton, IV et al. |
| 2019/0346670 A1 | 11/2019 | Stith et al. |
| 2019/0350448 A1 | 11/2019 | Kutsuma |
| 2019/0350449 A1 | 11/2019 | Tajima et al. |
| 2019/0351081 A1 | 11/2019 | Huber |
| 2019/0365204 A1 | 12/2019 | Lang et al. |
| 2019/0365213 A1 | 12/2019 | Park et al. |
| 2019/0366040 A1 | 12/2019 | Golden et al. |
| 2019/0374088 A1 | 12/2019 | Watanabe |
| 2019/0374091 A1 | 12/2019 | Somekawa |
| 2019/0374094 A1 | 12/2019 | Yamamoto |
| 2019/0374095 A1* | 12/2019 | Lord ............... A61B 1/00066 |
| 2019/0374129 A1 | 12/2019 | Palushi et al. |
| 2019/0374141 A1 | 12/2019 | Yamamoto |
| 2019/0380560 A1 | 12/2019 | Shijo |
| 2019/0380616 A1 | 12/2019 | Sidar et al. |
| 2019/0380617 A1 | 12/2019 | Oosake et al. |
| 2019/0387962 A1 | 12/2019 | Nakamitsu et al. |
| 2019/0388181 A1 | 12/2019 | Petersen et al. |
| 2020/0000320 A1 | 1/2020 | Tajima et al. |

(56) References Cited

U.S. PATENT DOCUMENTS

| | | |
|---|---|---|
| 2020/0000325 A1 | 1/2020 | Levy et al. |
| 2020/0000327 A1 | 1/2020 | Li |
| 2020/0000328 A1 | 1/2020 | Sakai et al. |
| 2020/0000330 A1 | 1/2020 | Ikeda et al. |
| 2020/0000438 A1 | 1/2020 | Yamamoto et al. |
| 2020/0005949 A1 | 1/2020 | Warkentine |
| 2020/0007829 A1 | 1/2020 | Miyahara |
| 2020/0008653 A1 | 1/2020 | Kamon |
| 2020/0008658 A1 | 1/2020 | Hayakawa |
| 2020/0008659 A1 | 1/2020 | Viebach et al. |
| 2020/0015657 A1 | 1/2020 | Garbin et al. |
| 2020/0016425 A1 | 1/2020 | Ding et al. |
| 2020/0022560 A1 | 1/2020 | Oosake |
| 2020/0022563 A1 | 1/2020 | Sugita |
| 2020/0029786 A1 | 1/2020 | Morimoto |
| 2020/0037850 A1 | 2/2020 | Akui |
| 2020/0037851 A1 | 2/2020 | Okita |
| 2020/0037856 A1 | 2/2020 | Watanabe |
| 2020/0037859 A1 | 2/2020 | Takemoto et al. |
| 2020/0037860 A1 | 2/2020 | Yamaya |
| 2020/0046201 A1 | 2/2020 | Ho et al. |
| 2020/0046202 A1 | 2/2020 | Morishima et al. |
| 2020/0046205 A1 | 2/2020 | Ueda |
| 2020/0046209 A1 | 2/2020 | Fancher |
| 2020/0046441 A1 | 2/2020 | Liu et al. |
| 2020/0054190 A1 | 2/2020 | Yoshida |
| 2020/0054194 A1 | 2/2020 | Melsheimer |
| 2020/0054195 A1 | 2/2020 | Akhoondi et al. |
| 2020/0054198 A1 | 2/2020 | Tseng |
| 2020/0054201 A1 | 2/2020 | Fujimori |
| 2020/0058693 A1 | 2/2020 | Suyama et al. |
| 2020/0059576 A1 | 2/2020 | Shimohata |
| 2020/0060514 A1 | 2/2020 | Sakamoto |
| 2020/0060517 A1 | 2/2020 | Roychowdhury et al. |
| 2020/0060518 A1 | 2/2020 | Roychowdhury et al. |
| 2020/0060520 A1 | 2/2020 | Sorensen et al. |
| 2020/0060521 A1 | 2/2020 | Sorensen |
| 2020/0060524 A1 | 2/2020 | Weitzner |
| 2020/0060526 A1 | 2/2020 | Toth et al. |
| 2020/0060528 A1 | 2/2020 | Akimoto |
| 2020/0060529 A1 | 2/2020 | Sorensen et al. |
| 2020/0069149 A1 | 3/2020 | Yanagihara |
| 2020/0069150 A1 | 3/2020 | Nakai et al. |
| 2020/0069152 A1 | 3/2020 | Kasumi |
| 2020/0069153 A1 | 3/2020 | Sueyasu |
| 2020/0069157 A1 | 3/2020 | Nakamoto |
| 2020/0069162 A1 | 3/2020 | Levy et al. |
| 2020/0069914 A1 | 3/2020 | Joo |
| 2020/0070482 A1 | 3/2020 | Attinger |
| 2020/0077869 A1 | 3/2020 | Ida |
| 2020/0077871 A1 | 3/2020 | Ogihara et al. |
| 2020/0077874 A1 | 3/2020 | Long et al. |
| 2020/0077880 A1 | 3/2020 | Ouyang et al. |
| 2020/0082529 A1 | 3/2020 | Mikami |
| 2020/0085283 A1 | 3/2020 | Salman et al. |
| 2020/0085284 A1 | 3/2020 | Piskun et al. |
| 2020/0090333 A1 | 3/2020 | Iwaki |
| 2020/0092526 A1 | 3/2020 | Sidar et al. |
| 2020/0107697 A1 | 4/2020 | Furukawa et al. |
| 2020/0107698 A1 | 4/2020 | Tatsuta et al. |
| 2020/0107699 A1 | 4/2020 | Ariyoshi |
| 2020/0112656 A1 | 4/2020 | Ho |
| 2020/0113412 A1 | 4/2020 | Jensen |
| 2020/0113415 A1 | 4/2020 | Kristensen |
| 2020/0113416 A1 | 4/2020 | Salman et al. |
| 2020/0113420 A1 | 4/2020 | Sato et al. |
| 2020/0113421 A1 | 4/2020 | Altshuler |
| 2020/0113423 A1 | 4/2020 | Yamazaki |
| 2020/0113426 A1 | 4/2020 | Ito et al. |
| 2020/0113555 A1 | 4/2020 | Ryan et al. |
| 2020/0120781 A1 | 4/2020 | Abraham et al. |
| 2020/0121165 A1 | 4/2020 | Nakao et al. |
| 2020/0121167 A1 | 4/2020 | Araki |
| 2020/0121169 A9 | 4/2020 | Lund et al. |
| 2020/0121171 A1 | 4/2020 | Kaye et al. |
| 2020/0121176 A1 | 4/2020 | Sidar et al. |
| 2020/0121218 A1 | 4/2020 | Sakai |
| 2020/0121304 A1 | 4/2020 | Johnsen et al. |
| 2020/0121360 A1 | 4/2020 | Opfermann et al. |
| 2020/0126223 A1 | 4/2020 | Kitamura et al. |
| 2020/0128214 A1 | 4/2020 | Tsuchiya et al. |
| 2020/0138266 A1 | 5/2020 | Suzuki et al. |
| 2020/0138267 A1 | 5/2020 | Tomura et al. |
| 2020/0138268 A1 | 5/2020 | Matthison-Hansen et al. |
| 2020/0138269 A1 | 5/2020 | Nishimura |
| 2020/0138270 A1 | 5/2020 | Wood et al. |
| 2020/0138272 A1 | 5/2020 | Neelamegam et al. |
| 2020/0138273 A1 | 5/2020 | Neelamegam et al. |
| 2020/0138274 A1 | 5/2020 | Aneja et al. |
| 2020/0138275 A1 | 5/2020 | Homma |
| 2020/0138276 A1 | 5/2020 | Aneja et al. |
| 2020/0138277 A1 | 5/2020 | Neelamegam et al. |
| 2020/0138419 A1 | 5/2020 | Aneja et al. |
| 2020/0142152 A1 | 5/2020 | Iguchi et al. |
| 2020/0142179 A1 | 5/2020 | Duckett, III |
| 2020/0144945 A1 | 5/2020 | Umemoto et al. |
| 2020/0146703 A1* | 5/2020 | Truckai .......... A61B 17/320758 |
| 2020/0154980 A1 | 5/2020 | Ben-Arye et al. |
| 2020/0154981 A1 | 5/2020 | Mankowski |
| 2020/0154982 A1 | 5/2020 | Niwa et al. |
| 2020/0163536 A1 | 5/2020 | Ponsky |
| 2020/0164186 A1 | 5/2020 | Terliuc et al. |
| 2020/0169686 A1 | 5/2020 | Amling et al. |
| 2020/0221926 A1 | 7/2020 | Petersen et al. |
| 2020/0221927 A1 | 7/2020 | Matthison-Hansen |
| 2020/0221929 A1 | 7/2020 | Harada |
| 2020/0221932 A1 | 7/2020 | Ouyang et al. |
| 2020/0221935 A1 | 7/2020 | Yamamoto et al. |
| 2020/0237185 A1 | 7/2020 | Do et al. |
| 2020/0237188 A1 | 7/2020 | Yan et al. |
| 2020/0237189 A1 | 7/2020 | Do et al. |
| 2020/0237201 A1 | 7/2020 | Mishima |
| 2020/0241280 A1 | 7/2020 | Satake et al. |
| 2020/0245853 A1 | 8/2020 | Wang et al. |
| 2020/0253460 A1 | 8/2020 | Yoshinaga et al. |
| 2020/0253461 A1 | 8/2020 | Wang et al. |
| 2020/0253463 A1 | 8/2020 | Kondo |
| 2020/0260937 A1 | 8/2020 | Zhou |
| 2020/0264424 A1 | 8/2020 | Hegenbarth et al. |
| 2020/0267292 A1 | 8/2020 | Matthison-Hansen et al. |
| 2020/0268235 A1* | 8/2020 | Chang .................. A61B 1/0052 |
| 2020/0275827 A1 | 9/2020 | Weise et al. |
| 2020/0281446 A1 | 9/2020 | Morimoto et al. |
| 2020/0281666 A1 | 9/2020 | Gunn et al. |
| 2020/0287899 A1 | 9/2020 | Koizumi et al. |
| 2020/0288946 A1 | 9/2020 | Takahashi |
| 2020/0294227 A1 | 9/2020 | Usuda |
| 2020/0297186 A1 | 9/2020 | Chiu et al. |
| 2020/0297188 A1 | 9/2020 | Ikeda |
| 2020/0297189 A1 | 9/2020 | Ikeda et al. |
| 2020/0297192 A1 | 9/2020 | Hanawa |
| 2020/0297193 A1 | 9/2020 | Takahashi et al. |
| 2020/0297422 A1 | 9/2020 | Gocho et al. |
| 2020/0305686 A1 | 10/2020 | Koyama |
| 2020/0305690 A1 | 10/2020 | Johnson et al. |
| 2020/0305691 A1 | 10/2020 | Morimoto et al. |
| 2020/0305692 A1 | 10/2020 | Wimmer et al. |
| 2020/0315428 A1 | 10/2020 | Harada |
| 2020/0315435 A1 | 10/2020 | Ratnakar |
| 2020/0315439 A1 | 10/2020 | Mizoguchi et al. |
| 2020/0315720 A1 | 10/2020 | Lwin et al. |
| 2020/0322512 A1 | 10/2020 | Aono et al. |
| 2020/0322538 A1 | 10/2020 | Haggerty et al. |
| 2020/0323418 A1 | 10/2020 | Narayana et al. |
| 2020/0323421 A1 | 10/2020 | Okaniwa et al. |
| 2020/0333581 A1 | 10/2020 | Sakai et al. |
| 2020/0336679 A1 | 10/2020 | Sachdev et al. |
| 2020/0337530 A1 | 10/2020 | Miller |
| 2020/0337538 A1 | 10/2020 | Ishikawa |
| 2020/0337539 A1 | 10/2020 | Shimohata et al. |
| 2020/0337540 A1 | 10/2020 | Takekoshi |
| 2020/0344386 A1 | 10/2020 | Yamamoto et al. |
| 2020/0359874 A1 | 11/2020 | Banik et al. |
| 2020/0359880 A1 | 11/2020 | Hiraoka |

(56) References Cited

U.S. PATENT DOCUMENTS

| | | |
|---|---|---|
| 2020/0397237 A1 | 12/2020 | Ulmschneider et al. |
| 2021/0022585 A1 | 1/2021 | Nishimura |
| 2021/0022587 A1 | 1/2021 | Meguro et al. |
| 2021/0022588 A1 | 1/2021 | Schultheis et al. |
| 2021/0022592 A1 | 1/2021 | Yamazaki |
| 2021/0093159 A1 | 4/2021 | Peterson et al. |
| 2021/0093162 A1 | 4/2021 | Sueyasu et al. |
| 2021/0093163 A1 | 4/2021 | Scutti et al. |
| 2021/0093164 A1 | 4/2021 | Iyoshi et al. |
| 2021/0093165 A1 | 4/2021 | Iyoshi et al. |
| 2021/0093166 A1 | 4/2021 | Shin et al. |
| 2021/0093169 A1 | 4/2021 | Ouyang et al. |
| 2021/0093174 A1 | 4/2021 | Kim et al. |
| 2021/0093175 A1 | 4/2021 | Sorensen et al. |
| 2021/0093224 A1 | 4/2021 | Morishima |
| 2021/0096309 A1 | 4/2021 | Miyawaki |
| 2021/0096351 A1 | 4/2021 | Mizoguchi et al. |
| 2021/0099645 A1 | 4/2021 | Ushijima et al. |
| 2021/0100578 A1 | 4/2021 | Weir et al. |
| 2021/0113057 A1 | 4/2021 | Oyama |
| 2021/0113059 A1 | 4/2021 | Kasumi |
| 2021/0113064 A1 | 4/2021 | Yoshinaga et al. |
| 2021/0113065 A1 | 4/2021 | Hosogoe |
| 2021/0113066 A1 | 4/2021 | Hosogoe |
| 2021/0113068 A1 | 4/2021 | Shin et al. |
| 2021/0113076 A1 | 4/2021 | Abe et al. |
| 2021/0116696 A1 | 4/2021 | Nakagawa et al. |
| 2021/0116697 A1 | 4/2021 | Krivopisk et al. |
| 2021/0145257 A1 | 5/2021 | Levinson |
| 2021/0145265 A1 | 5/2021 | Morishima et al. |
| 2021/0145267 A1 | 5/2021 | Duval |
| 2021/0204798 A1 | 7/2021 | Salman et al. |
| 2021/0204799 A1 | 7/2021 | Magno et al. |
| 2021/0204800 A1 | 7/2021 | Magno et al. |
| 2021/0204802 A1 | 7/2021 | Nir et al. |
| 2021/0205026 A1 | 7/2021 | Nakamitsu |
| 2021/0211586 A1 | 7/2021 | Suzuki et al. |
| 2021/0338045 A1 | 11/2021 | Crowley et al. |
| 2021/0338049 A1 | 11/2021 | Christensen |
| 2021/0338051 A1 | 11/2021 | Nielsen et al. |
| 2021/0338052 A1 | 11/2021 | Ouyang et al. |
| 2021/0338059 A1 | 11/2021 | Hosokai |
| 2021/0338062 A1 | 11/2021 | Do |
| 2021/0338355 A1 | 11/2021 | Yip et al. |
| 2021/0343779 A1 | 11/2021 | Fujimori |
| 2021/0344822 A1 | 11/2021 | Yoneyama |
| 2021/0344850 A1 | 11/2021 | Hale |
| 2022/0022727 A1 | 1/2022 | Oyama |
| 2022/0022732 A1 | 1/2022 | Do |
| 2022/0022733 A1 | 1/2022 | Horibe et al. |
| 2022/0030171 A1 | 1/2022 | Haggerty et al. |
| 2022/0104689 A1 | 4/2022 | Lang et al. |
| 2022/0109786 A1 | 4/2022 | Matsushita et al. |
| 2022/0160207 A1 | 5/2022 | Nycz et al. |
| 2022/0160210 A1 | 5/2022 | Jing et al. |
| 2022/0160212 A1 | 5/2022 | Cheon |
| 2022/0160213 A1 | 5/2022 | Uspenski et al. |
| 2022/0160215 A1 | 5/2022 | Katballe et al. |
| 2022/0160216 A1 | 5/2022 | Levy et al. |
| 2022/0160222 A1 | 5/2022 | Piskun et al. |
| 2022/0160366 A1 | 5/2022 | Kuhn |
| 2022/0175218 A1 | 6/2022 | Nishimura |
| 2022/0175219 A1 | 6/2022 | Schwarz |
| 2022/0175220 A1 | 6/2022 | Wood et al. |
| 2022/0175223 A1 | 6/2022 | Schwarz |
| 2022/0175224 A1 | 6/2022 | Sorensen et al. |
| 2022/0175225 A1 | 6/2022 | Schwarz |
| 2022/0175226 A1 | 6/2022 | Sorensen et al. |
| 2022/0192473 A1 | 6/2022 | Deng et al. |
| 2022/0192478 A1 | 6/2022 | Pollock et al. |
| 2022/0192479 A1 | 6/2022 | Harris et al. |
| 2022/0192781 A1 | 6/2022 | Yang |
| 2022/0225858 A1 | 7/2022 | Akui |
| 2022/0225862 A1 | 7/2022 | Onobori |
| 2022/0225864 A1 | 7/2022 | Konstorum et al. |
| 2022/0232170 A1 | 7/2022 | He et al. |
| 2022/0233054 A1 | 7/2022 | Hansen et al. |
| 2022/0233055 A1 | 7/2022 | Banik et al. |
| 2022/0233056 A1 | 7/2022 | Venkataraman |
| 2022/0233061 A1 | 7/2022 | Chen et al. |
| 2022/0233178 A1 | 7/2022 | Johnsen et al. |

FOREIGN PATENT DOCUMENTS

| | | |
|---|---|---|
| CN | 103417178 | 8/2016 |
| DE | 202010009234 U1 | 12/2011 |
| DE | 102018121711 | 9/2018 |
| EP | 3266365 | 1/2018 |
| JP | 2005-28018 A | 2/2005 |
| JP | 2006167221 | 6/2006 |
| KR | 102183544 | 11/2020 |
| WO | WO2006137255 | 6/2005 |
| WO | WO 2016/064449 A1 | 4/2016 |
| WO | WO 2018/098465 A1 | 5/2018 |
| WO | WO 2019/226307 | 11/2019 |
| WO | WO2020/006147 | 1/2020 |
| WO | WO2020/025960 | 2/2020 |

OTHER PUBLICATIONS

Supplementary EP Search Report for EP 17873945 dated Jun. 8, 2020.
English Translation of DE 202010009234U1.
English Translation of WO 2006137255.
Power Point Presentation: Gadgets, Devices & Tools for Endoscopy. NYSGA First Year Fellows Endoscopy Course 2018.
"Shear and Torsion", Roylance D, Jun. 23, 2000 [retrieved: Jan. 17, 2018], Retrieved from the internet: <URL: https://ocw.mit.edu/courses/materials-science-and-engineering/3-11-mechanics-of-materials-fall-1999/mc.
English abstract of CN 102740758 A obtained from Google Patents on Jul. 27, 2021.
English Translation JP2006167221, Retrieved Mar. 14, 2022 from Pat Docs.
English Translation of CH713337, Retrieved Mar. 14, 2022 from Pat Docs.
English Translation of CN 103417178.
English Translation of DE10218121711, Retrieved Mar. 14, 2022 from Pat Docs.
English Translation of KR102183544, Retrieved Mar. 14, 2022 from Pat Docs.

* cited by examiner

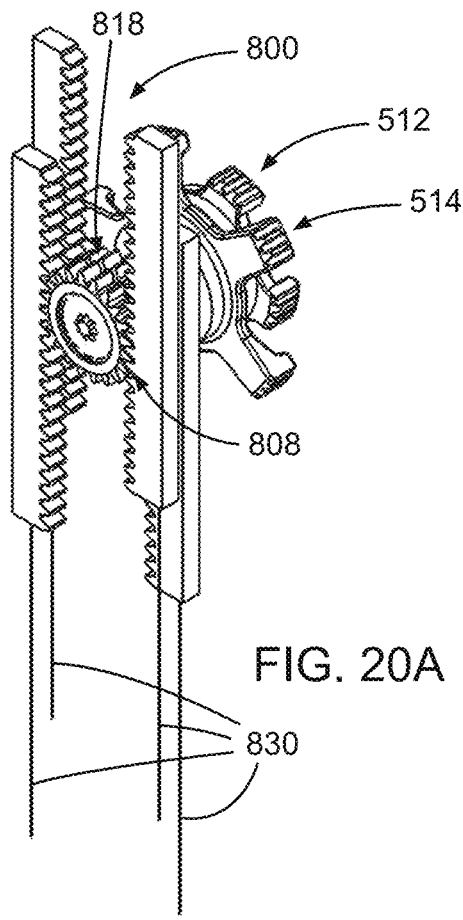
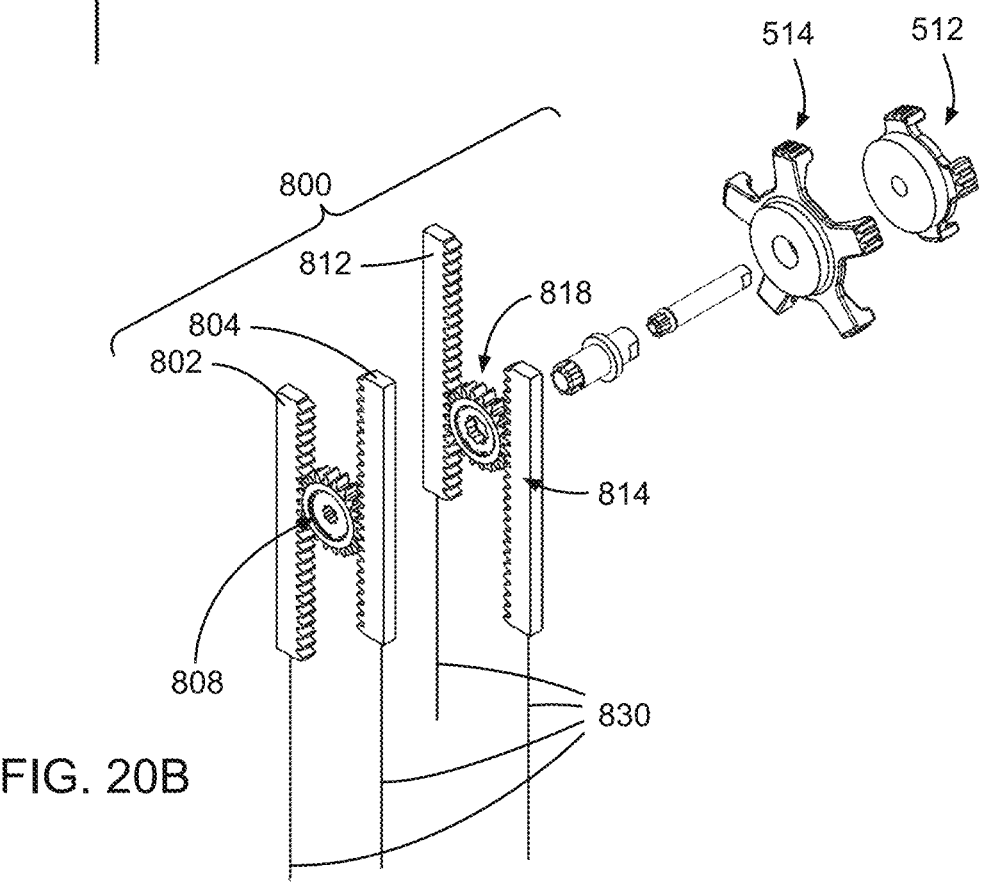
FIG. 20A
FIG. 20B

FIG. 25
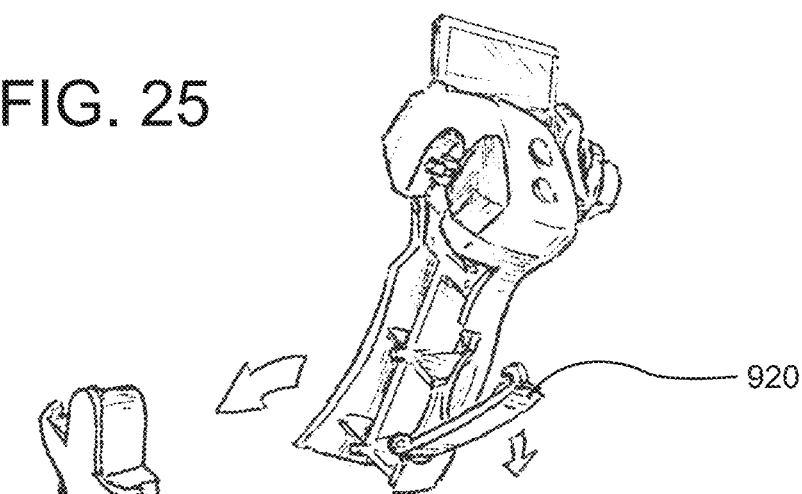
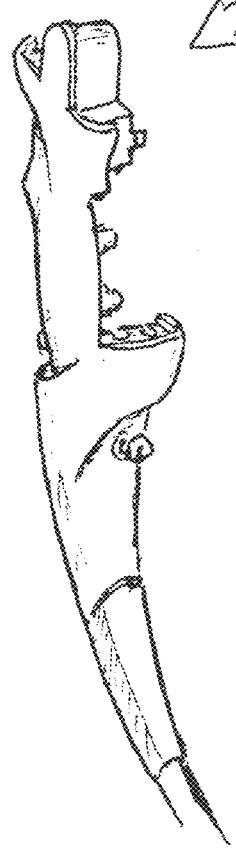
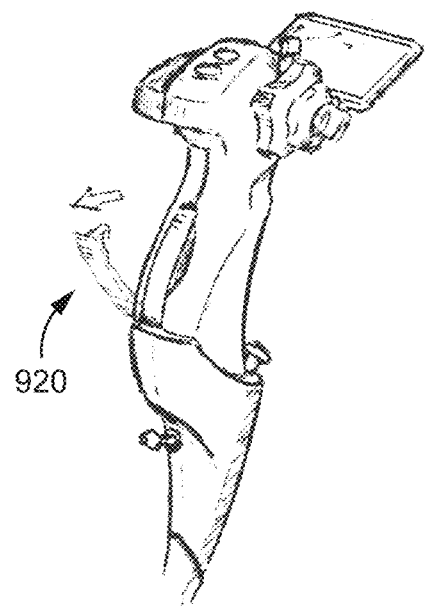
FIG. 26

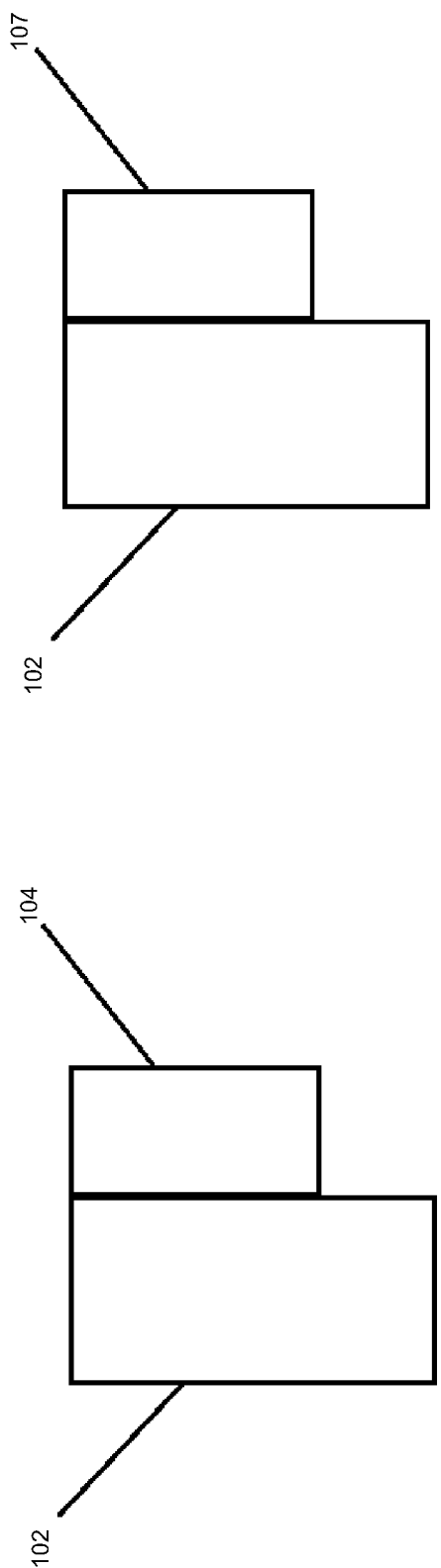

ined States Patent US 11,576,563 B2

ENDOSCOPE WITH SEPARABLE, DISPOSABLE SHAFT

FIELD OF THE INVENTION

This invention generally relates to endoscopes and, more particularly, to endoscopes used in gastroenterological applications.

BACKGROUND OF THE INVENTION

Endoscopes are used in a wide variety of medical procedures to visualize internal cavities or potential spaces within the human body during either diagnostic or therapeutic procedures.

One factor affecting endoscope design and use is infectious disease transmission. Although infectious disease transmission has always been a risk with reusable endoscopes, this risk has increased with the advent of antibiotic resistant bacteria. Once transmission of these bacteria has occurred between patients, antibiotic resistance makes it difficult to treat these infections. Many of these bacteria, including *Staphylococcus*, have the ability to form a protective outer barrier, frequently referred to as a bio-film, which protects the infectious bacteria from during cleaning procedures.

Another recent development that increases the risk of infectious disease transmission is an ever-increasing number of diagnostic procedures that require the use of smaller and more complicated instruments and longer working (lumens) and distal manipulators, e.g. elevators, associated with the endoscope distal articulating shaft. Together, the increasing prevalence of difficult to treat infectious diseases and more complex, difficult-to-clean endoscopes make the sterilization and re-use of endoscopes an increasingly risky activity.

Reducing or limiting the potential for infectious disease transmission is desirable. Accordingly, new endoscope designs are desired.

SUMMARY

The present disclosure pertains generally to endoscopes. In certain aspects, the present disclosure pertains to endoscopes having a reusable hand-piece removably coupled to a disposable shaft assembly. The reusable hand-piece includes articulation controls, and the disposable shaft assembly includes an articulation wire articulating assembly that engages the articulation controls when the reusable hand-piece and disposable shaft assembly are coupled to one another (e.g., when the housing of the reusable hand-piece and a housing of the disposable shaft assembly are coupled together).

The reusable hand-piece may have an optical and/or electrical connector that engages with a corresponding optical and/or electrical connector of the disposable shaft assembly when the reusable hand-piece is coupled to the disposable shaft assembly (e.g., when the housing of the reusable hand-piece and a housing of the disposable shaft assembly are coupled together). The optical and/or electrical connector of the reusable hand-piece may be part of an electronics module. The electronics module may include imaging controls.

The disposable shaft assembly can include an imaging device (e.g., image sensor such as CCD or CMOS sensor or a lens) and/or a light emitter (e.g., LED or a fiber optic cable). The imaging device and/or light emitter can be positioned at a distal end of the disposable shaft assembly.

The optical and/or electrical connectors can provide communication between the electronics module of the reusable hand-piece and the imaging device and/or the light emitter of the disposable shaft assembly.

The light emitter may include an element that produces light (e.g., an LED) or may communicate light provide proximally of the articulating distal portion. For example, the light emitter may be a light pipe (e.g., fiber optic cable). The imaging device may include a sensor that converts light into electrical signals (e.g., a CCD or a CMOS sensor) or a lens arranged to pass light from the articulating distal portion towards the proximal portion of the shaft.

The reusable hand-piece can include controls for controlling fluid flow through the disposable shaft assembly. Those controls can communicate with valves in the disposable shaft assembly and/or with external support equipment (e.g., pumps and/or valves in support equipment).

The endoscope assembly can include a coupler that holds the reusable hand-piece and the disposable shaft assembly together in the assembled configuration. The coupler can include a first portion on the reusable hand-piece and a second portion on the disposable shaft assembly, wherein the first and second portions of the coupler cooperate to hold the reusable hand-piece and the disposable shaft assembly together in the assembled configuration.

The coupler is actuatable to engage and/or disengage from the disposable shaft assembly. The coupler can include a latch having catch mounted on a pivoting and/or deflectable latch arm. The latch can be biased with a biasing member (e.g., spring) into a latching configuration that can hold the reusable hand-piece and disposable shaft assembly together. The coupler may include one or more magnets that hold the reusable hand-piece to the disposable shaft assembly when in the assembly configuration. The coupler can be arranged for actuation (e.g., to engage and/or disengage) without use of a hand tool (e.g., screwdriver). Preferably, the coupler is actuatable with fingers. The coupler can be defined by a portion of the housing of the reusable hand-piece and/or the disposable shaft assembly. For example, the housing may define a deflectable tab and/or a living hinge for the coupler.

The coupler can be arranged to indicate when the reusable hand-piece and the disposable shaft assembly are coupled to one another. For example, the coupler can provide an audible "click" when the reusable hand-piece and the disposable shaft assembly are coupled to one another.

The disposable shaft assembly can include one or more ports communicating with fluid flow paths (e.g., lumens) of a shaft of the disposable shaft assembly. The fluid flow paths may extend along a length of the shaft to one or more openings in at the distal end of the shaft. The fluid flow paths may be arranged for irrigation, insufflation, aspiration, and/or for receipt of a surgical tool (e.g., forceps, a cutter, and/or a ligation device). The reusable hand-piece may be absent of fluid flow paths and/or fluid connectors in fluid communication with fluid flow paths of the shaft.

The articulation controls of the reusable hand-piece can include articulation knobs. The articulation knobs can be arranged to receive articulation input from the user (e.g., in the form of rotational movement). The articulation knobs can communication with cams and/or gears of the separable disposable shaft to actuate control wires of the disposable shaft assembly. The user controlled articulation knobs can include two knobs having and/or rigidly attached to concentric drive shafts.

The concentric drive shafts each have a cam/gear engaging portion. This portion may have a non-circular cross-sectional geometric shape such that it is capable of transmitting torque. This geometric shape can include, but is not limited to, oval, spline, square, or star, just to name a few non-limiting examples.

Advantageously, the concentric shaft drive configuration permits attachment of the disposable shaft assembly to the reusable hand-piece without the need to orient the articulation knobs or the distal articulating tip to obtain a neutral reference position. Regardless of the orientation of the disposable shaft assembly (coiled or straight) at the time of attachment, the articulation knobs will freely rotate while the distal shaft (insertion tube) is manipulated prior to use by the clinician.

The disposable shaft assembly can include a cam/gear assembly support. For example, the disposable shaft assembly may have a proximal rigid housing having a surface that supports and positions the cams and/or gears of the disposable shaft assembly to receive the cam/gear engaging portions of the drive shafts. For example, the disposable shaft assembly may include a shelf upon which the cam/gear is positioned before and/or after the disposable shaft assembly is coupled to the reusable hand-piece (e.g., when the disposable shaft assembly is decoupled from the reusable hand-piece).

Each cam contained within the proximal rigid housing associated with the separable disposable shaft can have one or more circumferential grooves. These grooves can provide a track for the articulation wires. For example, each cam may be associated with a pair of opposing articulation wires. Each articulation wire can be rigidly fixed at one end to the cam and on the other end to the distal tip of the articulating section of the shaft. Rotation of the cam, such as by means of a user input torque applied to the corresponding knob, results in a tensile force applied to the articulating distal section.

A preferred embodiment utilizes two cams, each associated with a pair of articulation wires. Each pair of articulation wires provides means for articulating the distal shaft section in a single plane. Two pairs of articulation wires provide distal shaft articulation in two different plans that are perpendicular to one another, with a longitudinal axis of the proximal shaft portion passing through the intersection of the planes.

The mating features of the concentric drive shafts associated with the reusable hand-piece and the mating features of the cams associated with the separable, disposable shaft assembly are suitable for transmitting force in the form of torque applied to the articulation knobs to tensile force in the articulation wire(s) and corresponding movement of the distal shaft articulating section.

A portion of the drive shafts, such as the cam/gear engaging portions, may be tapered along a length of the drive shafts. For example, the drive shaft may have a portion taper from small to large in a direction towards the articulation knob. Advantageously, such an arrangement can aid in mating the drive shafts with the cam/gears of the disposable shaft assembly when the reusable hand-piece is coupled to the disposable shaft assembly.

The reusable hand-piece can include a clutch that applies an adjustable level of rotational resistance to the articulation control (e.g., articulation control knobs).

In arrangements disclosed herein, the articulation controls and electronics module are mounted to the housing of the reusable hand-piece, and the articulation wire actuating assembly and connector of the disposable shaft assembly are mounted to the housing of the disposable shaft assembly. Accordingly, separation of the housing of the reusable hand-piece from the housing of the disposable shaft assembly separates the articulation controls from the articulation wire actuating assembly and the electronics module from the connector of the disposable shaft assembly.

Advantageously, the reusable hand-piece of the endoscope assembly can remain entirely outside of the body of a patient during an endoscopic procedure while the disposable shaft assembly has a portion positioned within the body of the patient during the endoscopic procedure. Accordingly, the reusable hand-piece and disposable shaft assembly can be separated from one another after the procedure and the disposable hand-piece discarded (or reprocessed). As there are no fluid lumens of the reusable hand-piece that must be cleaned and sterilized, the cleaning (aka "reprocessing") effort between procedures is dramatically reduced. Additionally, as no portion of the reusable hand-piece, which is used for multiple patients, is inserted into the patient, the risk of infectious disease transmission can be dramatically reduced.

Disposable shaft assemblies can be arranged and/or provided in a variety of configurations to support upper and lower endoscopies. For example, disposable shaft assemblies may be arranged for colonoscope, gastroscope, sigmoidoscope, and/or duodenoscope procedures, just to name a few non-limiting examples. Additionally or alternatively, disposable shaft assemblies can be provided in various specialty configurations, e.g. pediatric insertion tube diameters. Advantageously, the ability to use the same reusable hand-piece for a variety of disposable shaft assemblies and/or procedures can substantially reduce capital investments by clinicians, clinician groups, and/or medical centers by eliminating the need to stock a plurality of dedicated scopes for each type of procedure, e.g. colonoscope, gastroscope, sigmoidoscope, duodenoscope, etc.

Methods of assembling an endoscope assembly, disassembling an endoscope assembly, and/or using an endoscope assembly are envisioned. Such methods can comprise connecting a housing of a reusable hand-piece to a housing of a disposable shaft assembly, wherein said reusable hand-piece has articulation controls and an electronics module and said disposable shaft assembly has an articulation wire actuating assembly and a connector; and wherein said connecting connects the articulation controls to the articulation wire actuating assembly and the electronics module to the connector of the disposable shaft assembly. Additionally, or alternatively, methods can comprise separating the housing of the reusable hand-piece from the housing of the disposable shaft assembly so as to separate the articulation controls from the articulation wire actuating assembly and the electronics module from the connector of the disposable shaft assembly. The methods can include providing a portion, or all, of any endoscope assembly described herein.

Advantageously, the systems, assemblies, devices, and methods disclosed herein can increase the quantity of endoscopy procedures that can be performed by a clinician and/or facility in a day by reducing and/or eliminating the time delays associated with existing reusable scopes that must undergo extensive reprocessing procedures (i.e., cleaning) between use. By using a disposable shaft, it is no longer necessary for the clinician and/or facility to reprocess (i.e., clean) the shaft and lumens of the shaft. Now the clinician and/or facility may simply wipe down the reusable hand-piece and connect a new, sterilized, disposable shaft assembly to the reusable hand-piece to prepare the endoscope assembly for another procedure.

Advantageously, the systems, assemblies, devices, and methods disclosed herein can allow a clinician to perform multiple and/or various procedures even without dedicated, reusable scopes and associated reprocessing equipment, supplies, and clean water. This can be particularly advantageous in battlefield settings or remote clinics with limited resources. In these cases, the reprocessing equipment, reprocessing supplies, trained reprocessing personnel, and reprocessing laboratory setting may not be available. Advantageously, the endoscopes disclosed herein can be prepared for a new procedure by simply using a wipe and antiseptic solution to clean the exterior surfaces of the reusable hand-piece and connecting a new disposable shaft assembly.

Advantageously, the reusable hand-piece can provide user-familiar-features using higher precision reliable components associated with the articulation knobs and the clutch.

Advantageously, incorporating the articulation handles and clutch into the reusable hand-piece reduces the components of the separable disposable shaft assembly thus resulting in a lower cost disposable portion of the endoscope.

The proximal rigid housing associated with the separable disposable shaft assembly can also include features for managing lumens for tool, irrigation, and aspiration. These features may either secure fabricated connectors or incorporate features for connecting to external devices and tubing. Advantageously, incorporating these lumen and connector features into the proximal rigid housing of the separable disposable shaft can reduce and/or prevent infectious disease transmission by segregating potential bodily fluid contact surfaces to the separable disposable shaft assembly.

In another embodiment of the endoscope, the reusable hand-piece incorporates a battery, a control board, and a transmitter (e.g., a wireless transmitter) for transmitting image data to an external storage device.

Advantageously, the incorporation of a power supply (battery), control board, and transmitter facilitates patient and image data storage and sharing while simplifying the components associated with the separable disposable shaft.

The reusable hand-piece can include a circuit board (controller) arranged to control at least a portion of support equipment (e.g., one or more pumps and/or valves in support equipment). One or more switches of the re-usable hand-piece can be associated with the circuit board so as to control the support equipment. Advantageously, such an arrangement can eliminate the need for valves for the irrigation and aspiration lumens to be physically associated with the reusable hand-piece and/or the separable distal shaft assembly.

The arrangements disclosed herein can utility low cost, miniature high-resolution cameras. Advantageously, the low cost of the components can allow for disposable endoscopes that satisfy cost, dimensional, and resolutions requirements set forth by health care providers and/or insurers.

The disposable shaft assemblies disclosed herein can be intended for one-time-use. Advantageously, a disposable medical device can reduce transmission of infectious diseases.

Applicant has also observed that expertise associated with the assessment of particular diseases and the performance of novel therapeutic procedures has become increasingly concentrated at clinical research institutions or larger healthcare facilities. Advantageously, the endoscopes disclosed herein can facilitate the dissemination of patient and image data.

The inventive aspects and embodiments discussed herein may be used independently or in combination with each other.

Other aspects, objectives, and advantages of the present disclosure will become more apparent from the following detailed description when taken in conjunction with the accompanying drawings.

BRIEF DESCRIPTION OF THE DRAWINGS

In the drawings:

FIG. 20A depicts a rear, isometric view of an articulation assembly;

FIG. 20B depicts a rear, partially-exploded, isometric view of the articulation assembly of FIG. 20A;

FIG. 25 depicts a perspective view of an endoscope assembly having a latch, with the reusable hand-piece detached from the disposable shaft assembly;

FIG. 26 depicts a perspective view of the endoscope assembly of FIG. 25;

FIG. 29A depicts a diagrammatic view of the endoscope assembly with the reusable hand-piece attached to a first disposable shaft assembly.

FIG. 29B depicts a diagrammatic view of the endoscope assembly with the reusable hand-piece attached to a second disposable shaft assembly.

While the invention will be described in connection with certain preferred embodiments, there is no intent to limit it to those embodiments. On the contrary, the intent is to cover all alternatives, modifications, and equivalents as included within the spirit and scope of the invention as defined by the appended claims.

DETAILED DESCRIPTION OF THE INVENTION

Figure 1:
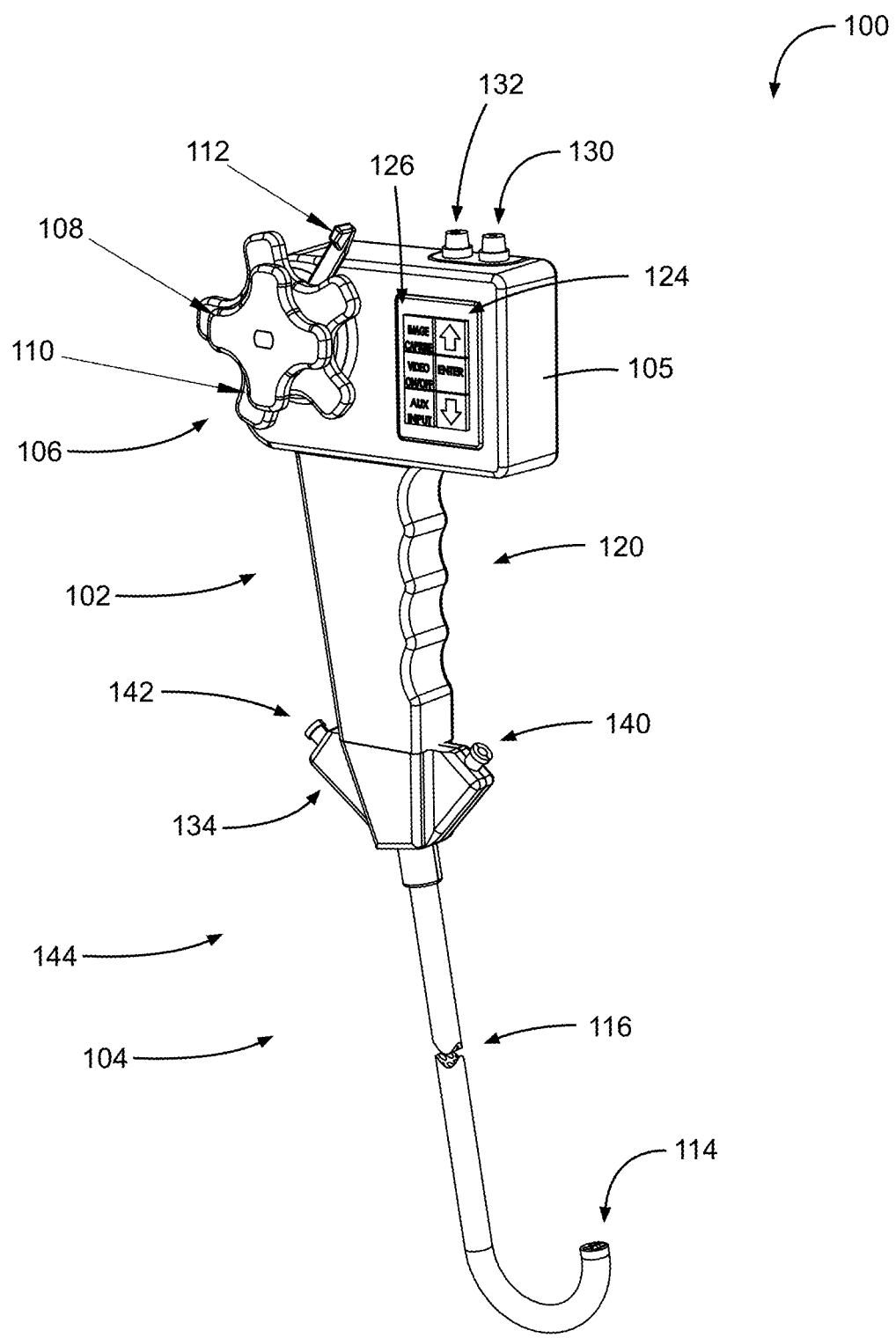
FIG. 1 depicts a front isometric view of a first embodiment of an endoscope assembly.
Figure 2D:
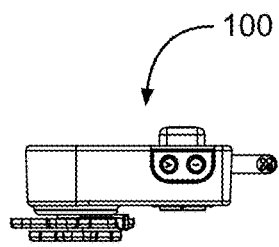
FIG. 2D depicts a top view of the endoscope assembly of FIG. 1.
Figure 2A:
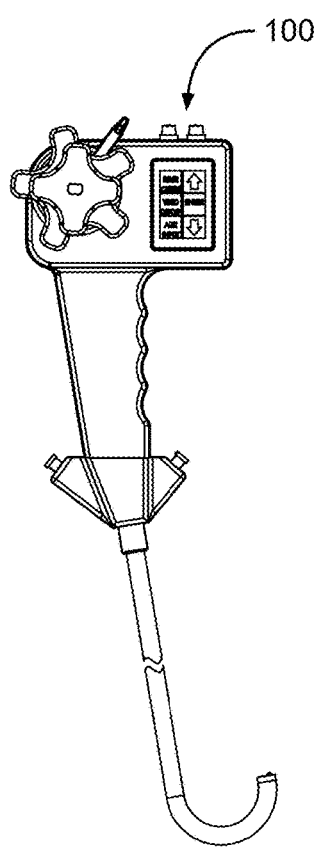
FIG. 2A depicts a front view of the endoscope assembly of FIG. 1.
Figure 2B:
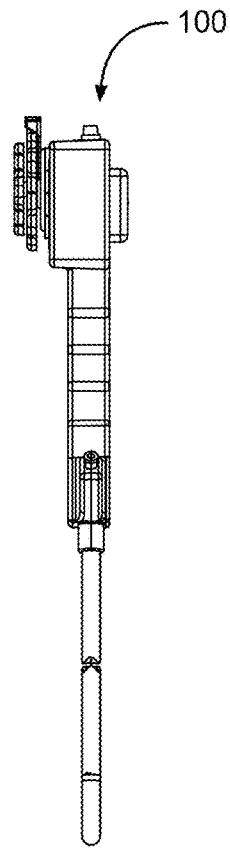
FIG. 2B depicts a right side view of the endoscope assembly of FIG. 1.
Figure 2C:
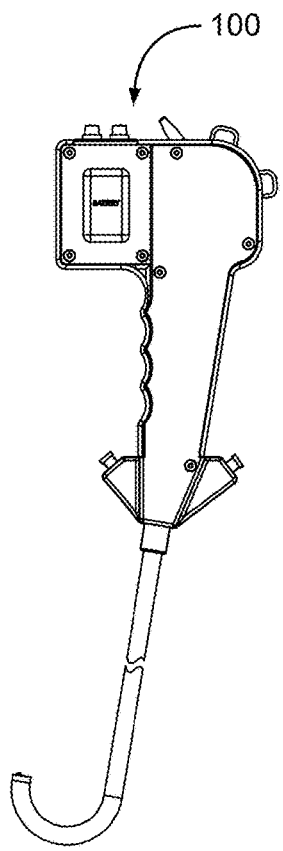
FIG. 2C depicts a rear view of the endoscope assembly of FIG. 1.

FIG. 1 depicts an endoscope assembly 100. The endoscope assembly comprises a reusable hand-piece 102 removably coupled to a disposable shaft assembly 104. The reusable hand-piece includes a housing 105 supporting an articulation control 106, such as a first articulation control knob 108 and a second articulation control knob 110. The first articulation control knob can have a smaller maximum cross-sectional dimension (e.g., diameter) than the second articulation control knob.

The articulation control can include an articulation clutch 112. The articulation clutch can be controlled by the user to apply a selectable level of resistive torque to prevent unintended rotation of a control knob, which may articulate the articulating distal portion 114 of the shaft 116 of the disposable shaft assembly.

The housing of the reusable hand-piece can include a handle portion 120. The handle portion is arranged to be gripped by a user's hand during operation of the endoscope assembly.

An image controller 124 can be mounted to the housing of the reusable hand-piece and arranged to control the image generated by the endoscope assembly. The image controller can include controls 126 (e.g., buttons) for image capture and/or recording video from the endoscope assembly.

Controls (e.g., buttons) for controlling irrigation, suction, insufflation, and/or irrigation can be mounted to the housing of the reusable hand piece. For example, one of buttons 130 and 132 may be arranged for irrigation and the other for aspiration.

The separable disposable shaft assembly can include a rigid housing 134 having fluid connectors, such as ports 140 and 142, located near a proximal end 144 of the shaft. The fluid connectors can communicate with one or more lumens of the shaft so as to allow for a tool and/or fluid to pass through the fluid connector(s) and into the lumen(s). For example, the separable disposable shaft may have fluid connectors communicating with irrigation, insufflation, and/or aspiration/suction lumens of the shaft. The fluid connectors may be male and/or female Luer connectors.

Figure 3:
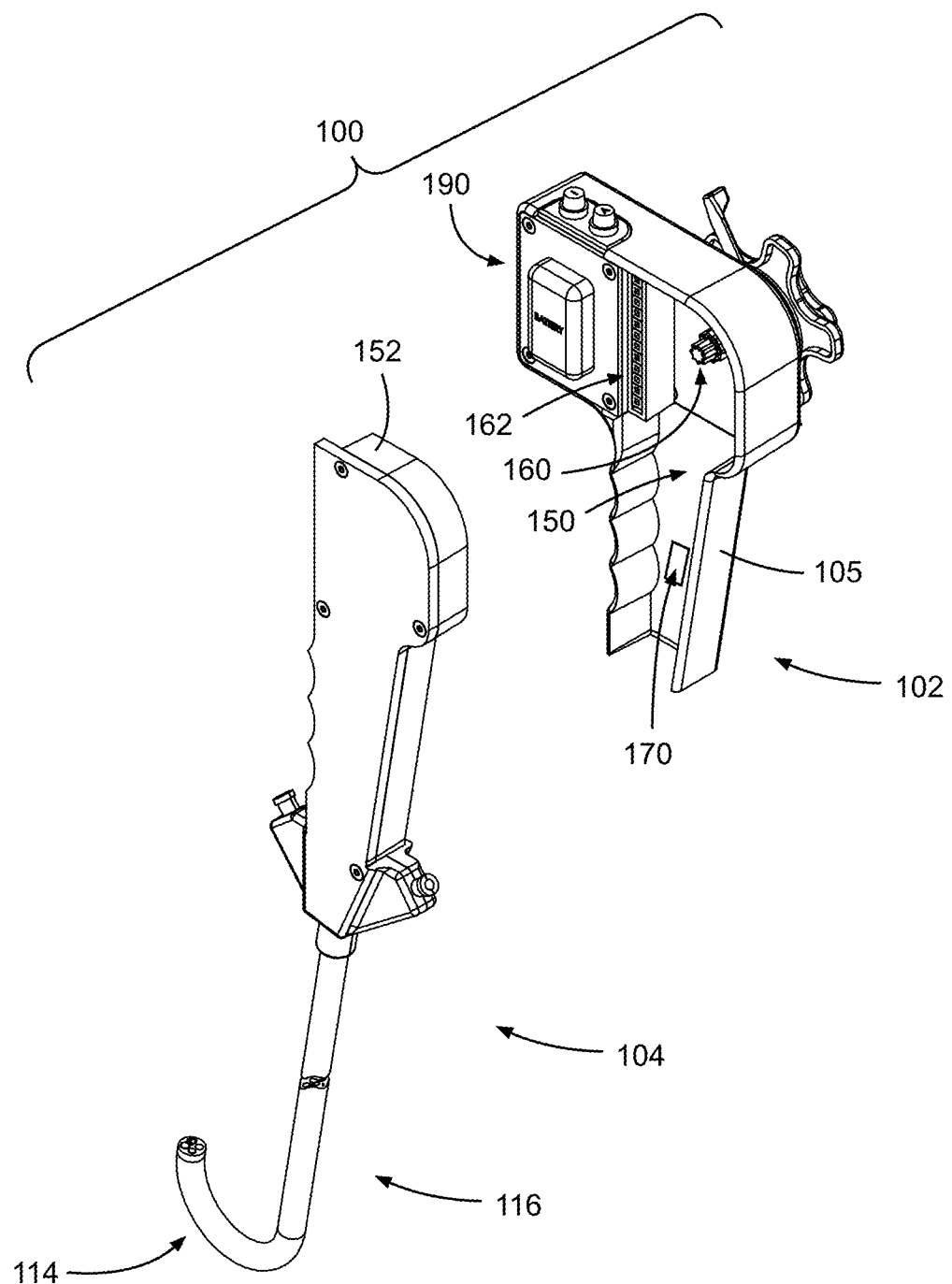
FIG. 3 depicts a rear, partially-exploded isometric view of the endoscope assembly of FIG. 1.

FIG. 3 illustrates the endoscope assembly with the reusable hand-piece disconnected from the disposable shaft assembly. In the illustrated embodiment, the housing of the reusable hand-piece supports drive shafts 160 connected to the articulation control. The drive shafts extend into the region of the reusable hand-piece that receives the disposable shaft assembly. For example, the housing of the reusable hand-piece can define a recess 150 that receives a portion 152 of the disposable shaft assembly when the disposable shaft assembly and reusable hand-piece are connected to one another. Drive shafts 160 of the articulation control can extend into the recess such that, when the reusable hand-piece and the disposable shaft assembly are joined together, the drive shafts engage the disposable shaft assembly. The recess may include an optical and/or electrical connector 162 for optically and/or electrically connecting the reusable hand-piece to the disposable shaft assembly.

A coupler for removably coupling the reusable hand-piece to the disposable shaft assembly can be mounted to the housing reusable hand-piece. The coupler is arranged to engage a portion of the disposable shaft assembly when the disposable hand-piece is connected to the disposable shaft assembly. For example, the coupler may include a latch and/or a magnet 170, just to name a few non-limiting examples, that cooperate(s) with a portion of the disposable shaft assembly to hold the reusable hand-piece and the disposable shaft assembly together.

Figure 4:
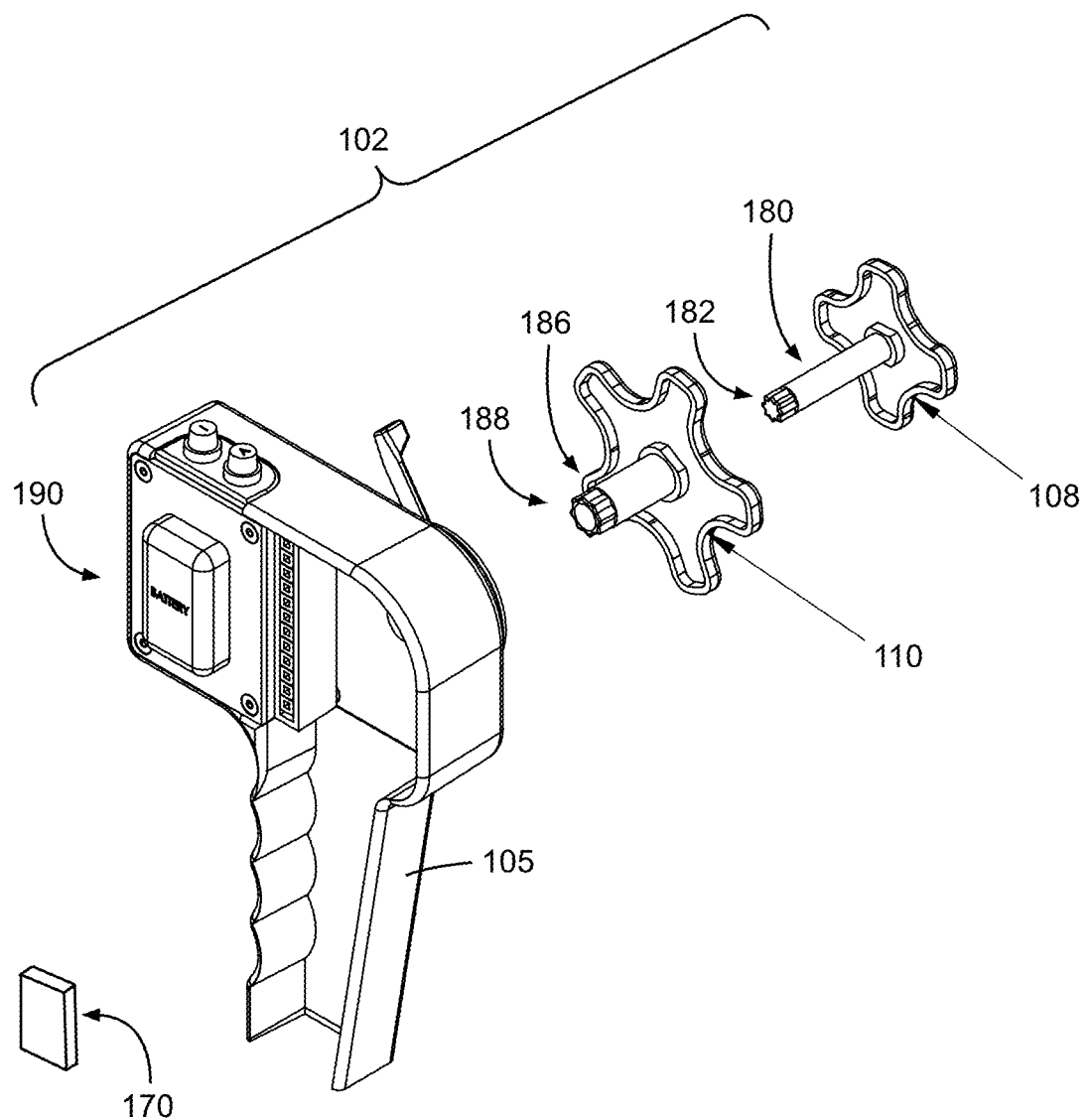
FIG. 4 depicts a rear, partially-exploded isometric view of the reusable hand-piece of FIG. 1.
Figure 5:
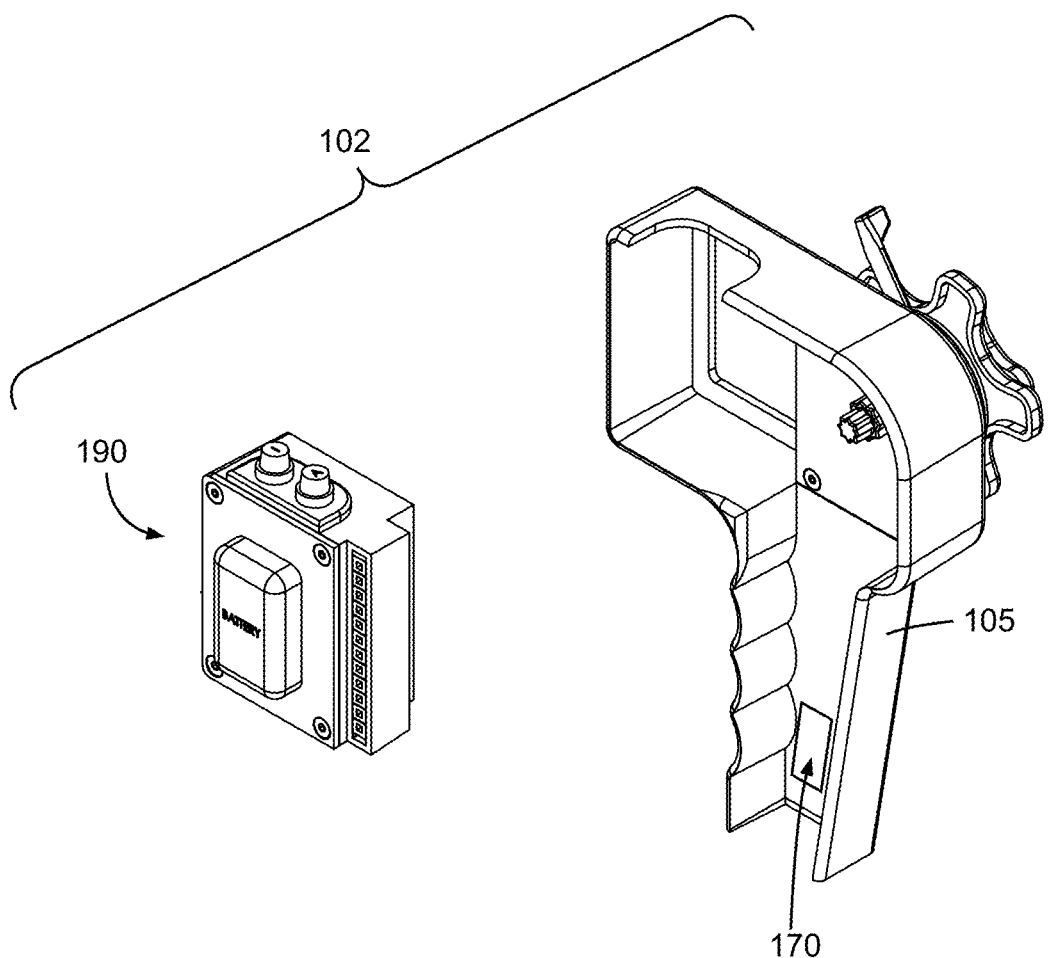
FIG. 5 depicts a rear, partially-exploded isometric view of the reusable hand-piece of FIG. 1.
Figure 6:
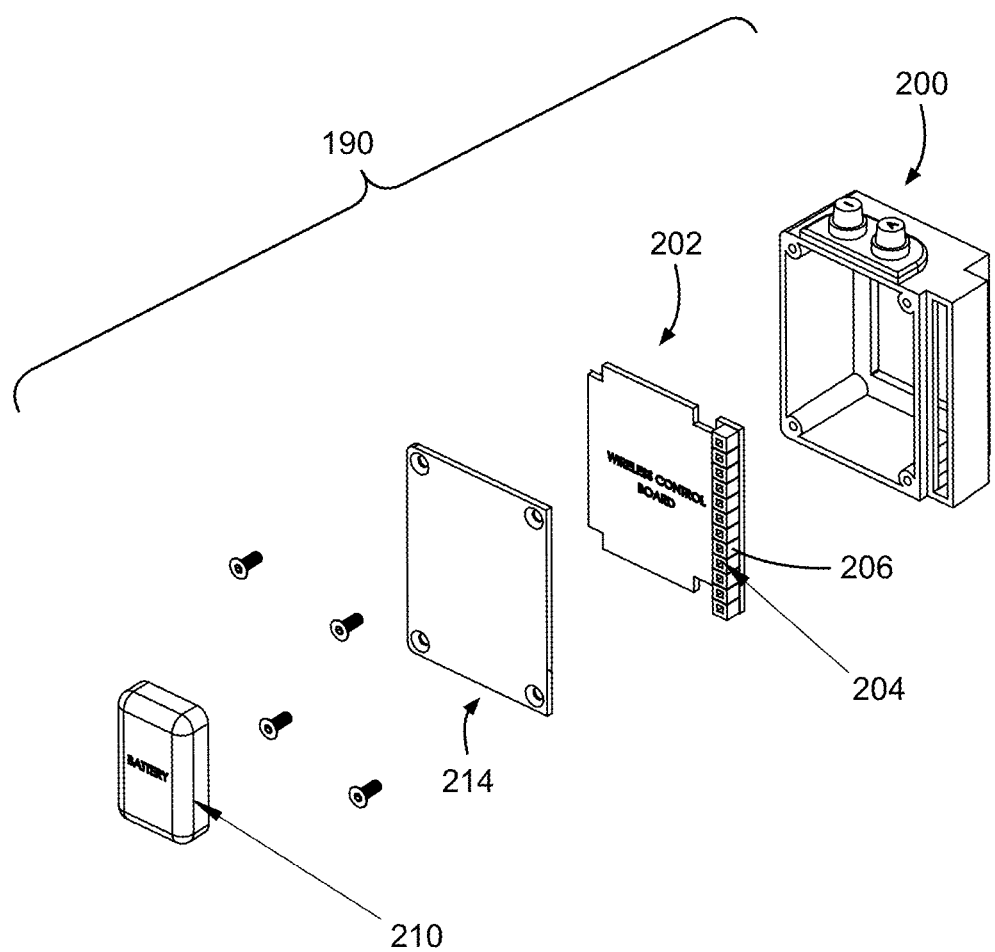
FIG. 6 depicts a rear, exploded isometric view of the electronics module.

As shown in FIGS. 3 and 4, the first articulation knob can have or be connected to a first drive shaft 180 having a cam/gear engaging portion 182 and the second articulation knob can have or be connected to a second drive shaft 186 having a cam/gear engaging portion 188. The drive shafts can be concentric drive shafts. For example, as shown in the illustrated embodiment, the first drive shaft can extend through the second drive shaft such that the cam/gear engaging portions are exposed when in the assembled configuration. Accordingly, the first drive shaft can have a smaller maximum cross-sectional dimension (measured orthogonal to the axis of the drive shaft) and a greater length than the second drive shaft.

An electronics module 190 can be mounted to the housing of the reusable hand-piece. The electronics module can include controls (e.g., 126, 130, and/or 132), discussed above, of the reusable hand-piece. The electronics module can include a housing 200 supporting a circuit board 202. The circuit board can have a wireless transmitter and/or receiver arranged for wireless communication.

The electronics module includes an optical and/or electrical connector 204 arranged to optically and/or electrically connect the electronics module to the reusable hand-piece and/or the disposable shaft assembly. For example, the circuit board may include terminals 206. The terminals can provide electrical connectivity to corresponding terminals of the disposable shaft assembly, such as signal/power terminals located on a disposable shaft assembly housing.

The electronics module can include a battery 210. The battery can be a removable battery that is removably mountable on a battery mount 214 that electrically connects the battery to the electronics module. For example, the battery mount may provide electrical connectivity between the battery and the circuit board.

Figure 7A:
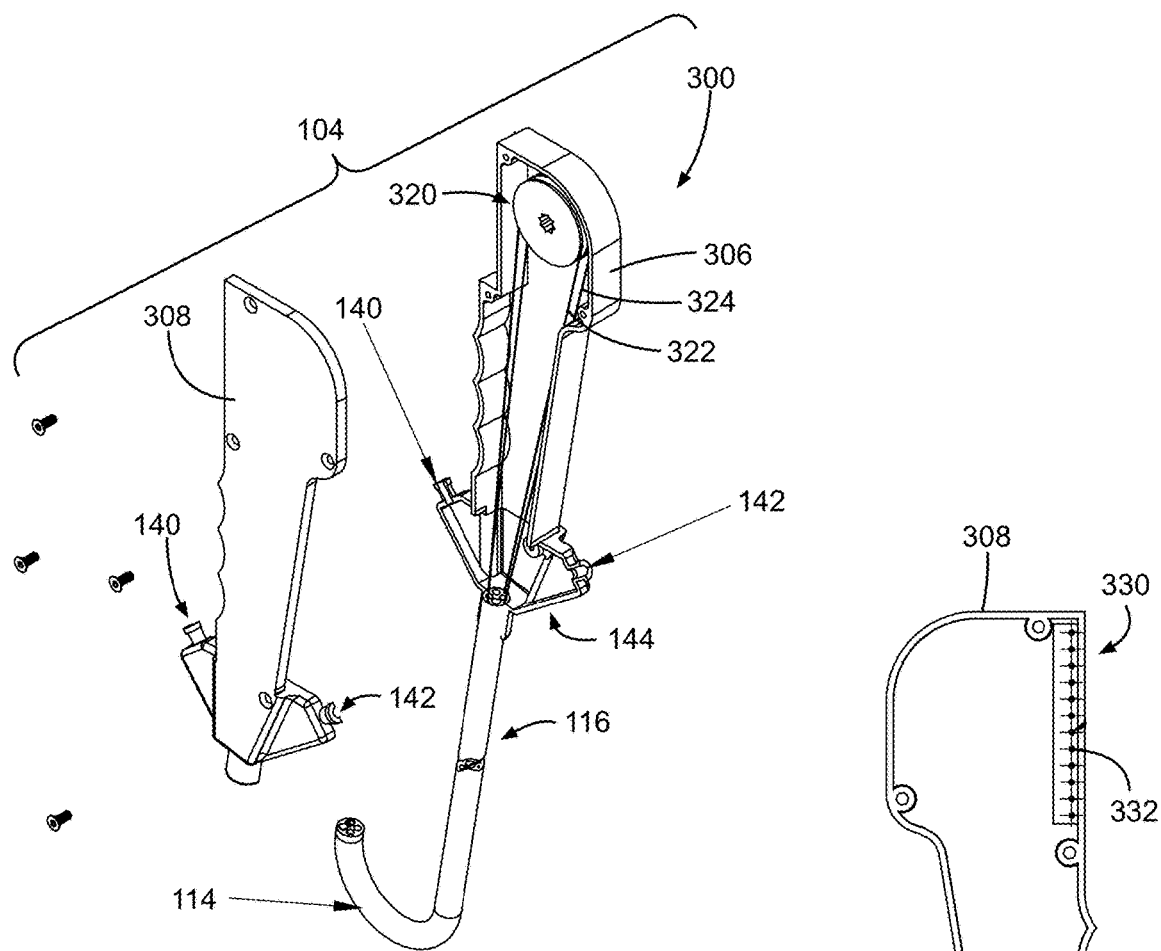
FIG. 7A depicts a rear, partially exploded isometric view of the disposable shaft assembly of FIG. 1.
Figure 7B:
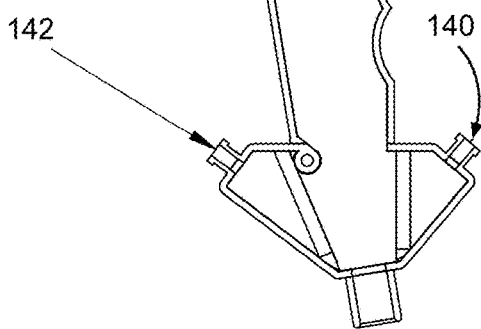
FIG. 7B depicts a front view of the second housing portion.
Figure 8:
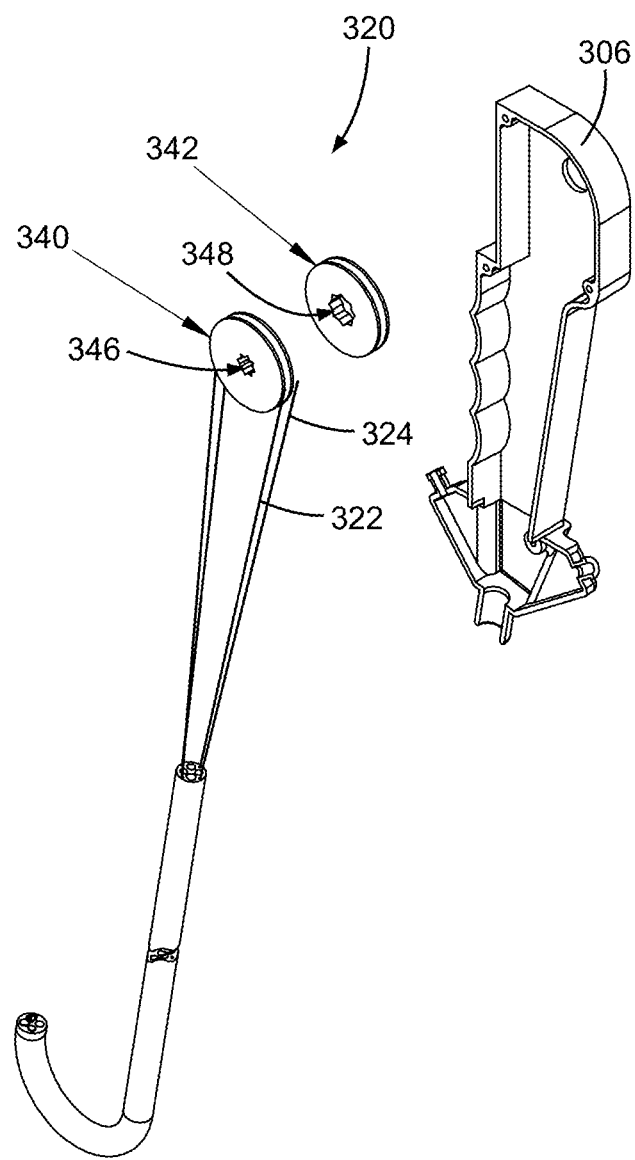
FIG. 8 depicts rear, exploded, isometric view of the separable disposable shaft without the second housing portion.
Figure 9:
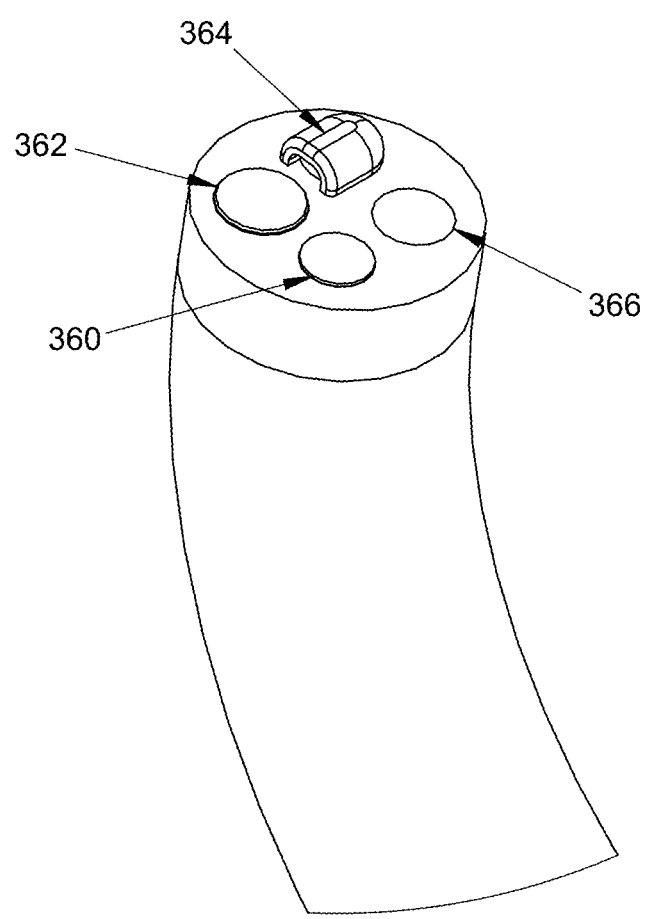
FIG. 9 depicts the distal end of the disposable shaft assembly.
Figure 10:
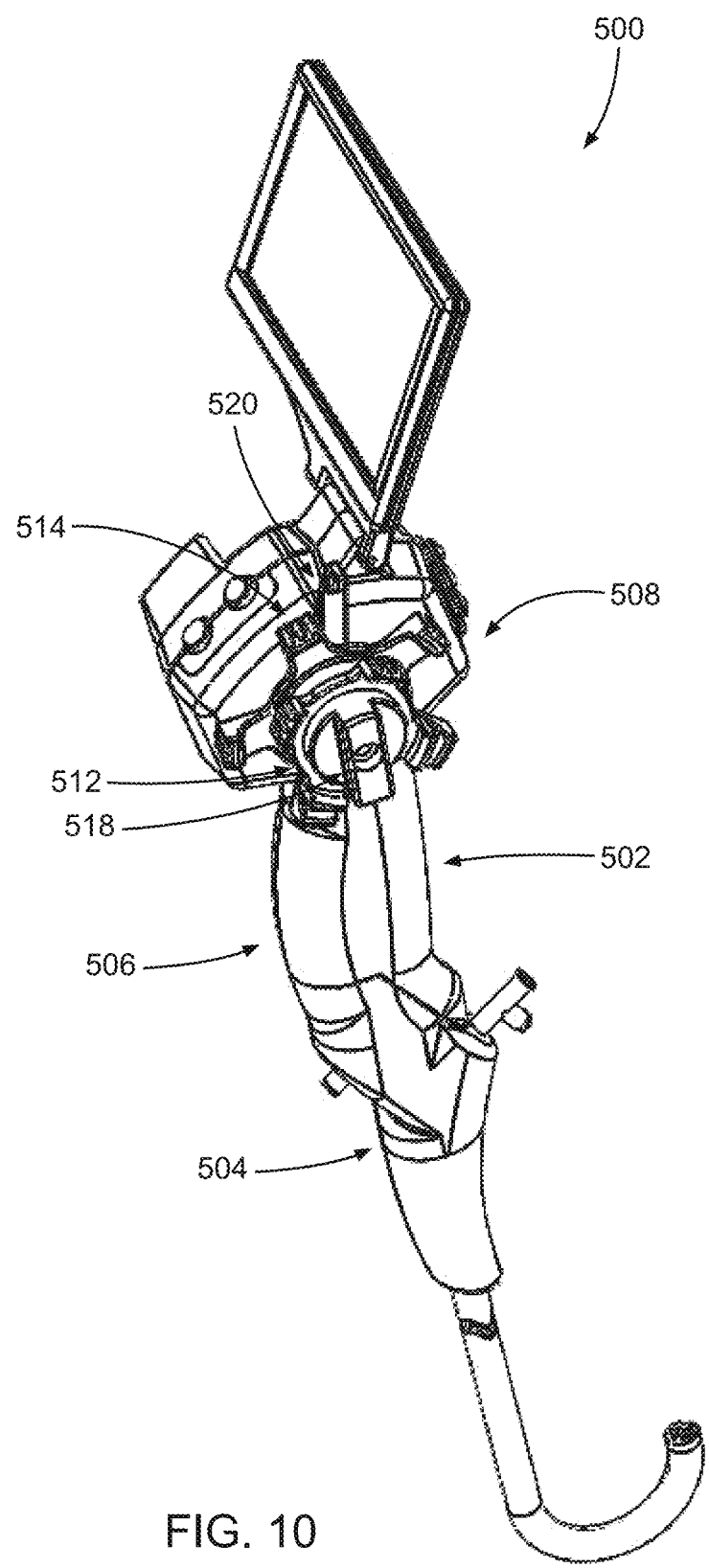
FIG. 10 depicts a front isometric view of a second embodiment of an endoscope assembly.
Figures 11A, 11B:
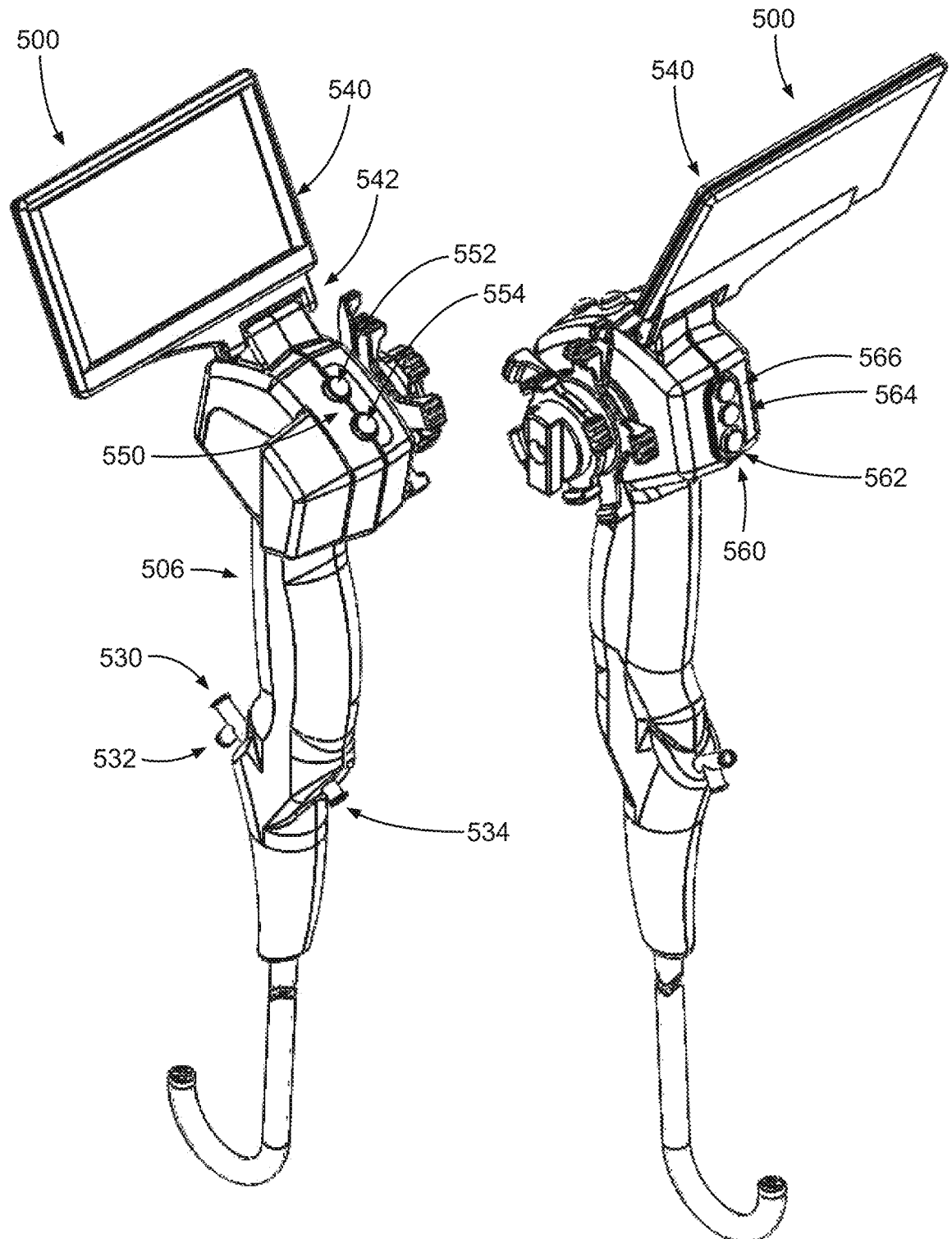
FIG. 11A depicts a rear isometric view of a second embodiment of the endoscope assembly of FIG. 10.
FIG. 11B depicts a front isometric view of a second embodiment of the endoscope assembly of FIG. 10.
Figure 12A:
FIG. 12A depicts a front view of the endoscope assembly of FIG. 10.
Figure 12B:
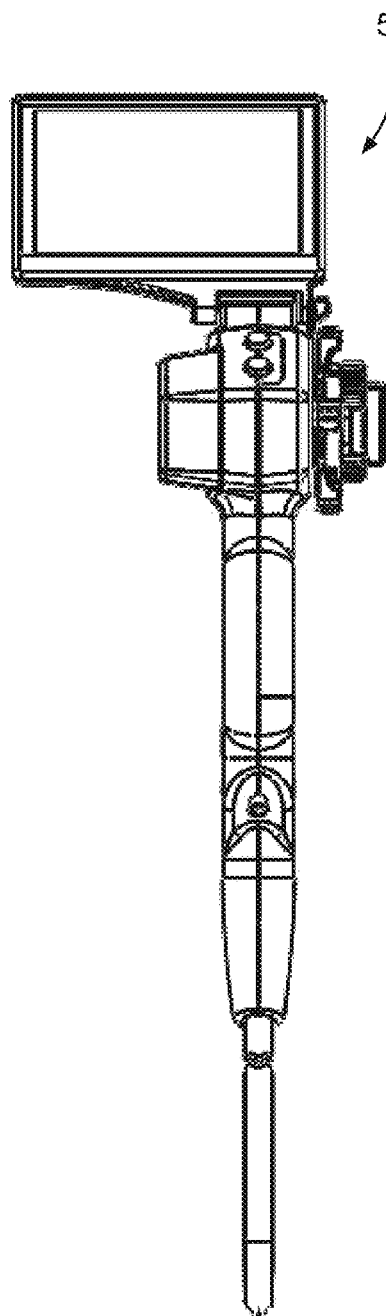
FIG. 12B depicts a left side view of the endoscope assembly of FIG. 10.
Figure 12C:
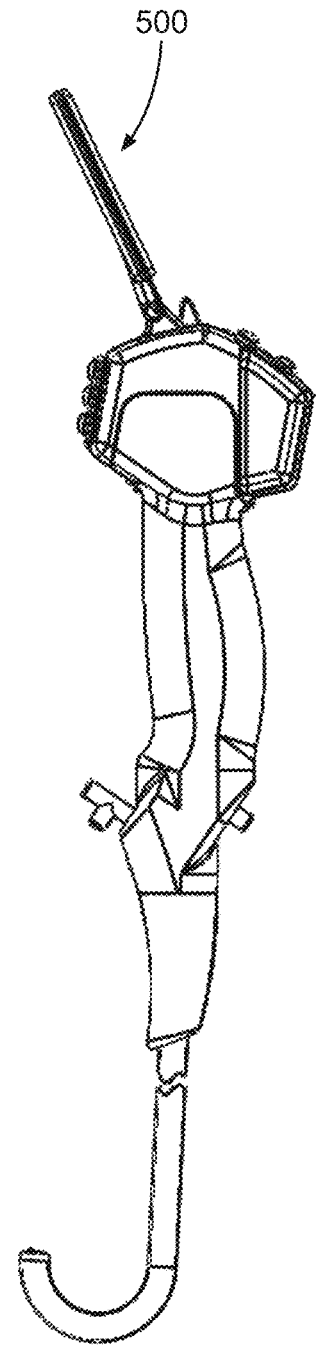
FIG. 12C depicts a rear view of the endoscope assembly of FIG. 10.
Figure 12D:
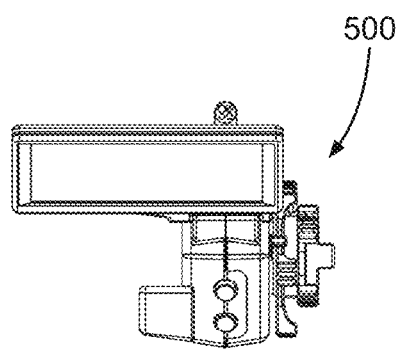
FIG. 12D depicts a top view of the endoscope assembly of FIG. 10.
Figure 13:
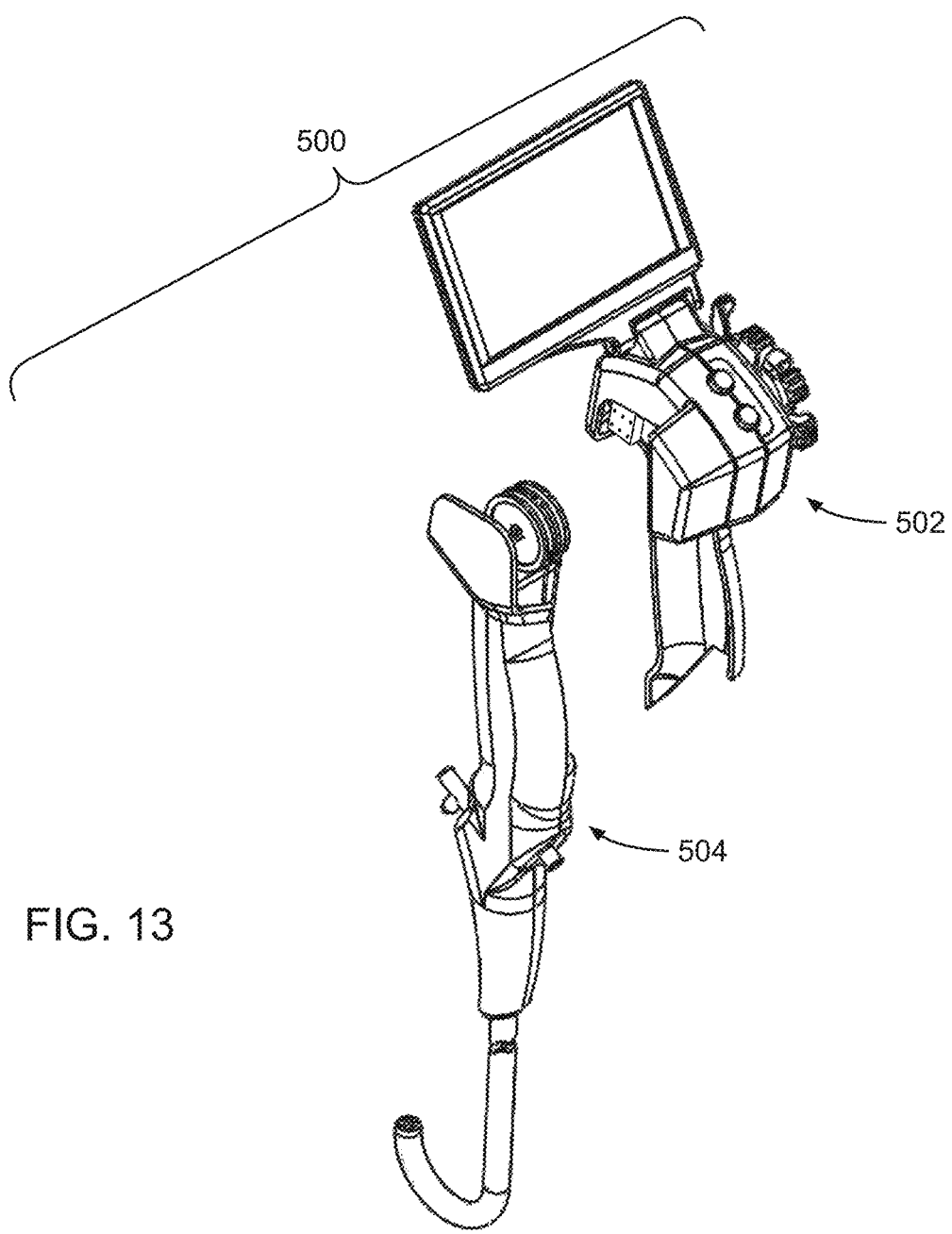
FIG. 13 depicts a rear, partially-exploded isometric view of the endoscope assembly of FIG. 10.
Figure 14:
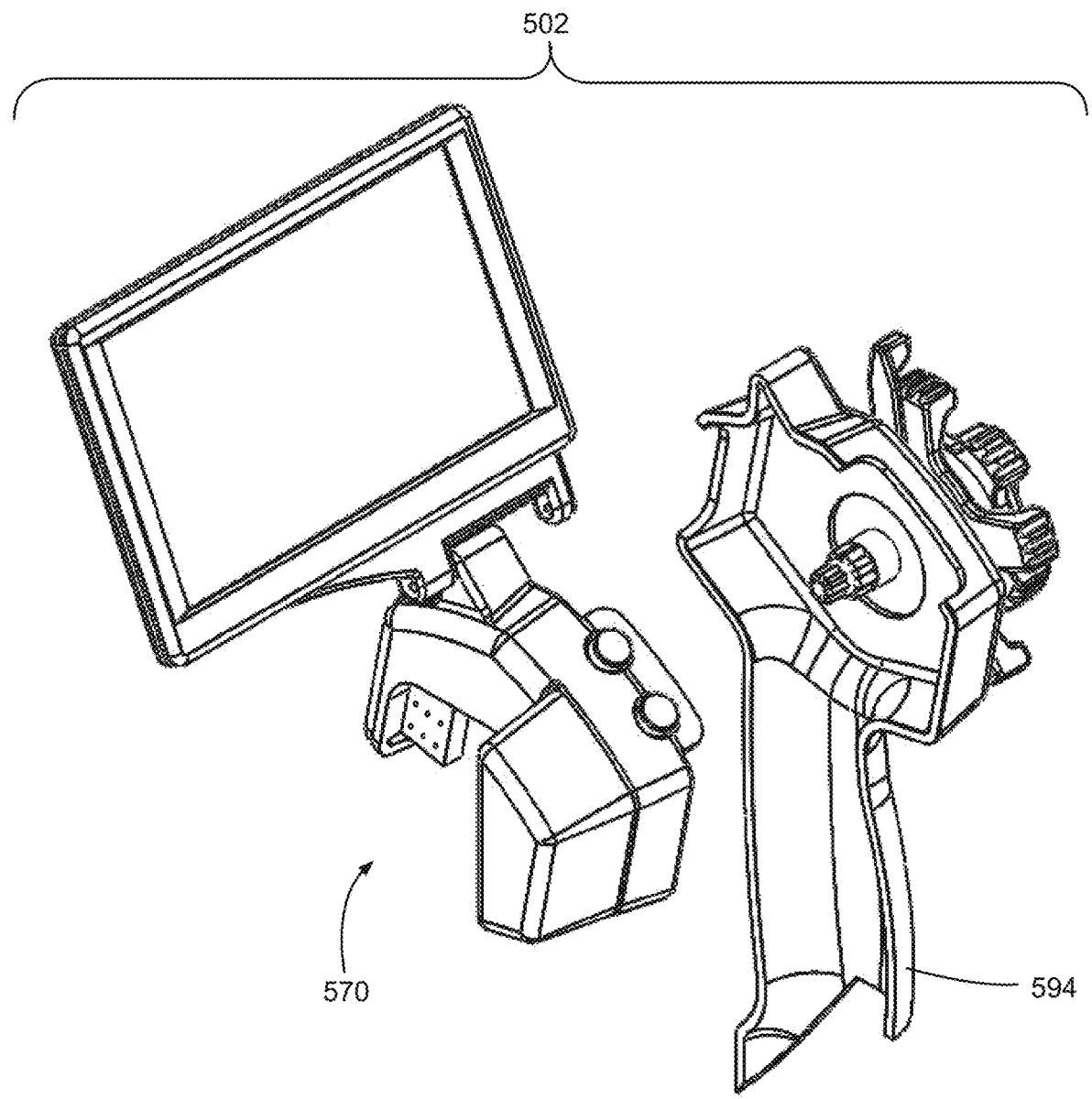
FIG. 14 depicts a rear, partially-exploded isometric view of the reusable hand-piece of FIG. 10.
Figure 15:
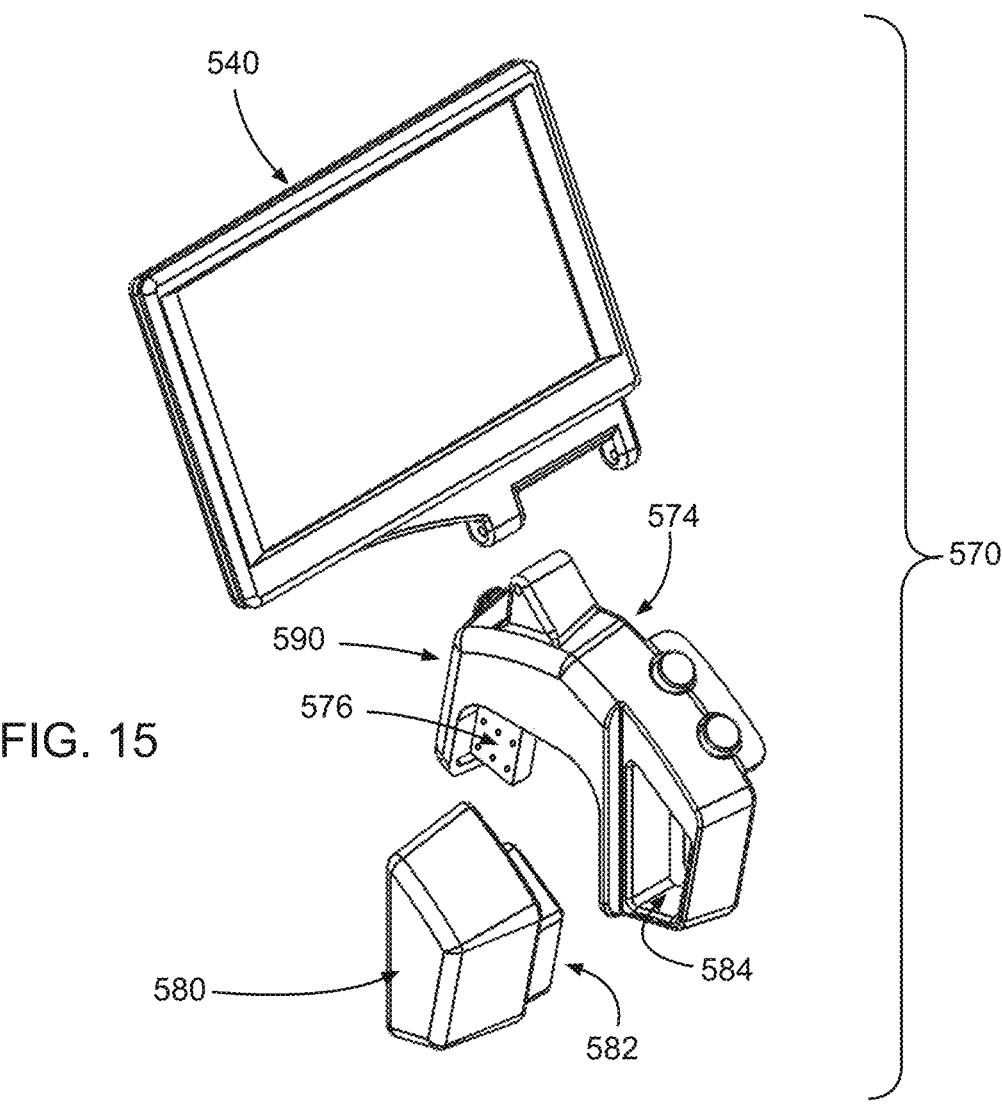
FIG. 15 depicts a rear, partially-exploded isometric view of the electronics module.
Figure 16:
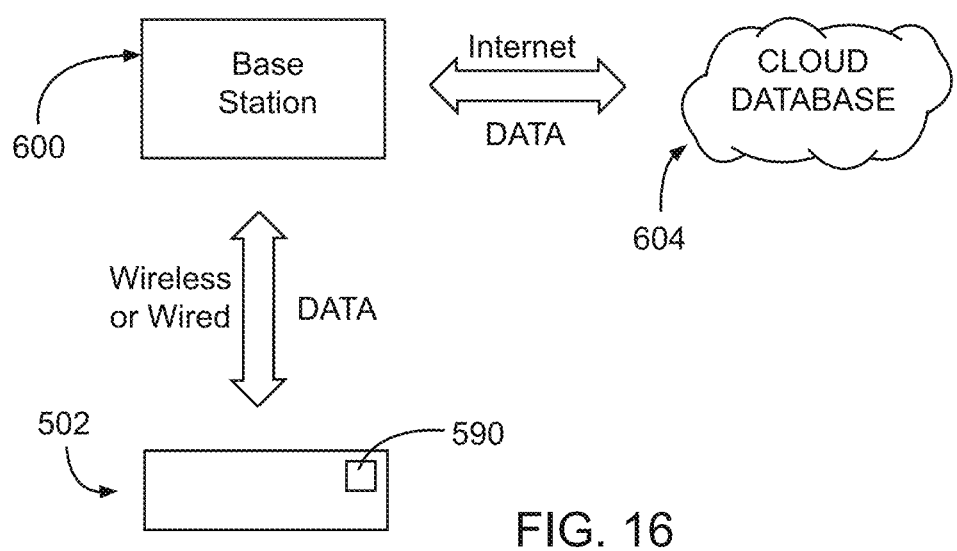
FIG. 16 depicts communication of the endoscope assembly with a base station and remote storage.
Figure 17:
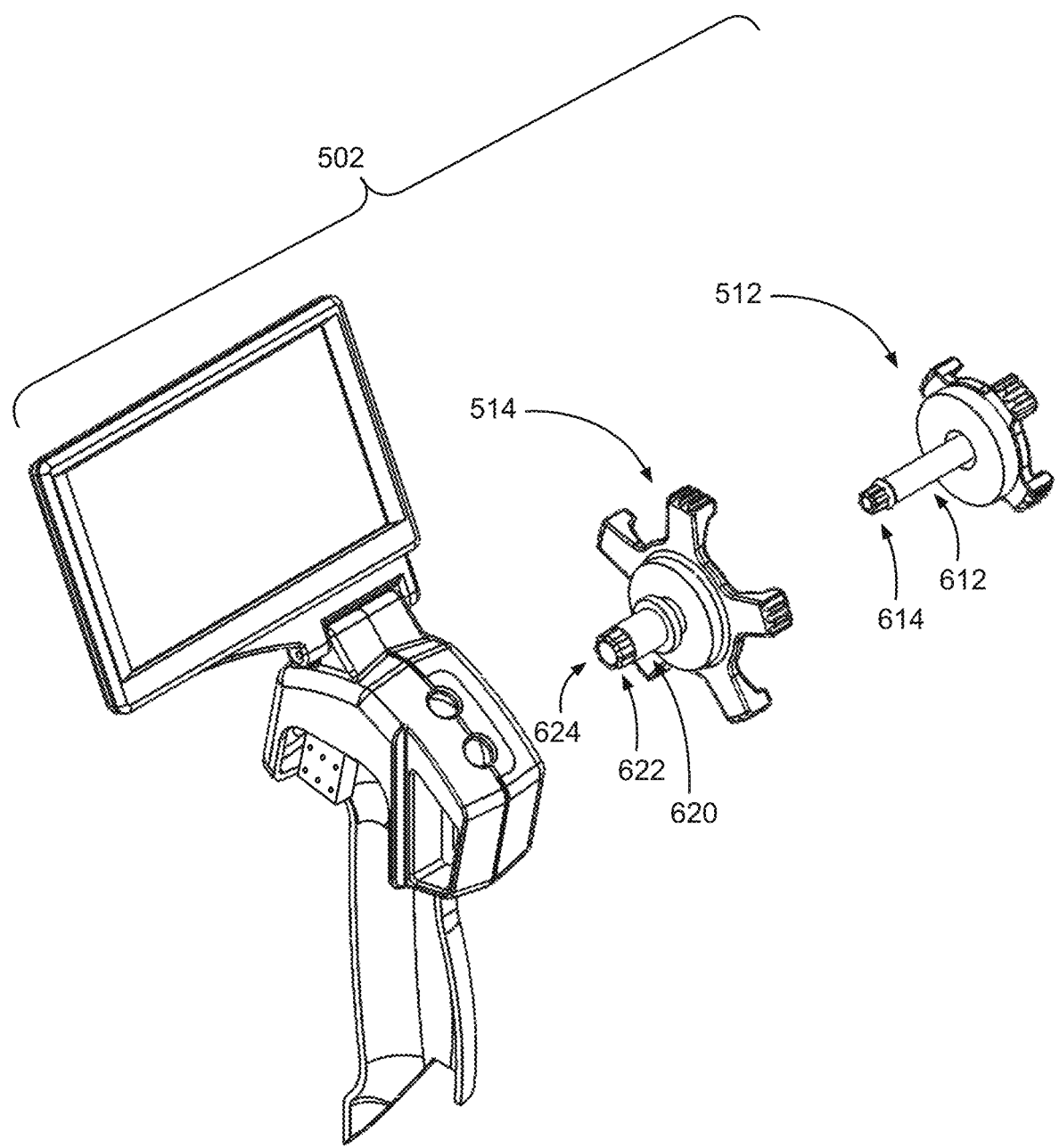
FIG. 17 depicts a rear, partially exploded isometric view of the reusable hand-piece.

Turning now to FIGS. 7-9, the disposable shaft assembly includes a housing 300 located at a proximal end 144 of the shaft. The housing can include a first housing portion 306 and a second housing portion 308. The first housing portion of the disposable shaft assembly supports an articulation wire actuating assembly, such as a cam assembly 320, attached to a plurality of articulation wires, such as first articulation wire 322 and second articulation wire 324. The articulation wires extend from the articulation wire actuating assembly to the articulating distal portion 114 of the shaft 116 and, upon rotation of portions of cam assembly, articulate (e.g., deflect) the articulating distal portion.

An optical and/or electrical connector 330 arranged to optically and/or electrically connect the disposable shaft assembly to the reusable hand-piece is mounted to the housing of the disposable shaft assembly (e.g., the second housing portion). For example, the disposable shaft assembly can include prongs 332 that contact terminals of the reusable hand-piece when the housing of the reusable hand-piece and the housing of the disposable shaft assembly are connected.

Optical and/or electrical conductors (not shown) connect the optical and/or electrical connector of the housing to shaft. For example, electrical conductors may extend from the prongs 332 to the proximal portion of the shaft so as to allow electrical communication between the optical and/or electrical connector and a light emitter and/or a CCD/CMOS sensor positioned at the distal tip of the shaft.

As mentioned above, the disposable shaft assembly includes fluid connectors such as ports 140 and 142. The fluid connectors can be defined by the housing assembly or attached to the housing assembly. Fluid tubing, not shown, connects the lumens of the fluid connectors to lumens of the shaft. Accordingly, fluid transferred through the shaft does not contact portions of the reusable hand-piece.

The cam assembly, shown in FIG. 8, includes a first cam 340 and a second cam 342. A first articulation wire (or pair of articulation wires) is attached to the first cam, and a second articulation wire (or pair of articulation wires) is attached to the second cam. The first cam defines a recess 346 that receives the cam engaging portion of the first drive shaft, and the second cam defines a recess 348 that receives the cam engaging portion of the second drive shaft when the reusable hand-piece and the disposable shaft assembly are connected together. In this way, rotation of an articulation control knob can rotate the connected cam and actuate an articulation wire. In the illustrated embodiment, the first articulation wire is arranged to actuate the articulating distal portion in a first plane when actuated, and the second articulation wire is arranged to articulate the articulating distal portion in a second plane when actuated. The first and second planes can be orthogonal to one another.

FIG. 9 illustrates the distal end of the articulating distal portion of the shaft. The distal end can include a light emitter 360, an imaging device 362, a first opening 364 to an irrigation or aspiration lumen of the shaft, and a second opening 366 to a lumen of the shaft, such as one that is arranged to receive a tool (e.g., forceps, a cutter, and/or a ligation device).

FIGS. 10-13 illustrate another endoscope assembly 500. The endoscope assembly includes a reusable hand-piece 502 removably attachable to a disposable shaft assembly 504. The reusable hand-piece includes a handle 506 and an articulation control 508. The articulation control can include a first articulation knob 512 and a second articulation control knob 514.

When the reusable hand-piece is connected to the disposable shaft assembly, the first articulation control knob can control articulation of a articulating distal portion of the disposable shaft assembly in a first plane (e.g., left/right) and the second articulation control knob can control articulation in a second plane (e.g., up/down). The first and second planes can be orthogonal to one another.

The articulation control can include a clutch for adjusting the resistance required to actuate portions of the articulation control. For example, the articulation control can include a first clutch 518 arranged to selectively adjust rotational resistance of the first articulation control knob and a second clutch 520 arranged to selectively adjust the rotational resistance of the second articulation control knob.

The disposable shaft assembly can include one or more ports providing access to one or more lumens of the articulating distal portion of the shaft. For example, the disposable shaft assembly can include an instrument port 530, a suction port 532, and/or an inflation/irrigation port 534.

A display 540 can be mounted to the housing of the reusable hand-piece. The display can be a touchscreen display. The display can be connected to the housing of the hand-piece via a hinge 542 so that the display is pivotable relative to the handle of the hand-piece.

Imaging controls 550 can be mounted to the housing of the reusable hand-piece. For example, the reusable hand-piece can include an image capture switch 552 and/or a video capture switch 554. The imaging controls can be positioned at a first location on the hand-piece, such as above the handle of the reusable hand-piece so that, when the handle is being gripped in a hand of an operator, the imaging controls can be actuated by at least one finger (e.g., thumb) of the hand gripping the handle.

One or more fluid control switches 560 for controlling the passage of fluid(s) through the disposable shaft assembly can be mounted to the housing of the reusable hand-piece. For example, the hand-piece can include an inflation switch 562, an irrigation switch 564, and a suction switch 566. Fluid control switches can be positioned at a second location on the hand-piece, the second location being remote from the first location, such as on a forward surface of the hand-piece. The fluid control switches are located so that, when the handle is being gripped in the hand of the operator, the fluid control switches can be actuated by at least one finger (e.g., the index finger) of the hand gripping the handle. Preferably, the fluid control switches are positioned so as to be operable by a first finger and the imaging controls are positioned so as to be operable by a second finger of an operator's hand gripping the handle. Advantageously, such an arrangement can allow for one-handed, simultaneous, and independent operation of the imaging controls and fluid control switches.

An electronics module 570 can be mounted to the housing of the reusable hand-piece. The display, the imaging controls, and/or the fluid control switches discussed above may be attached to and/or included in the electronics module. The electronics module can include a controller 574 having an optical and/or electrical connector 576 (e.g., terminals). The optical and/or electrical connector is arranged to connect to a connector of the disposable shaft assembly for the transmission of light and/or electricity from the controller to the disposable shaft assembly.

The controller of the reusable hand-piece can be arranged to receive a battery 580. Preferably, the battery is removably mountable on the controller. For example, the battery can have a portion 582 that is removably mountable on a battery mounting portion 584 of the controller so that the battery can be removed from the controller to be replaced and/or recharged.

The controller may include a communication module 590 arranged for wireless and/or wired communication with a base station 600. The communication module may communicate using a wireless communication protocol such as 802.11 a/b/g/n and/or Bluetooth®. Data, such as image and/or video data, may be communicated between the controller and the base station.

The base station may communicate with a remote database 604. The remote database may be connected to the internet (e.g., the world wide web) and the base station and remote database capable of communicating with one another using TCP/IP.

The controller can be mounted to a housing 594 that supports the articulation controls of the reusable hand-piece. The housing can define at least a portion of the handle.

The articulation controls of the reusable hand-piece can include drive shafts for transmitting torque to the disposable shaft assembly. For example, the first articulation control knob may include a first drive shaft 612 having a first torque-transmitting feature 614 and the second articulation control knob may include a second drive shaft 620 having a second torque-transmitting feature 622.

The drive shafts of the articulation controls may be concentric. For example, the second drive shaft may define an opening 624 arranged to receive the first drive shaft so that the first drive shaft can extend through the second drive shaft and the first and second torque-transmitting features be presented to the disposable shaft assembly when the endoscope assembly is in an assembled configuration.

Figures 18A, 18B:
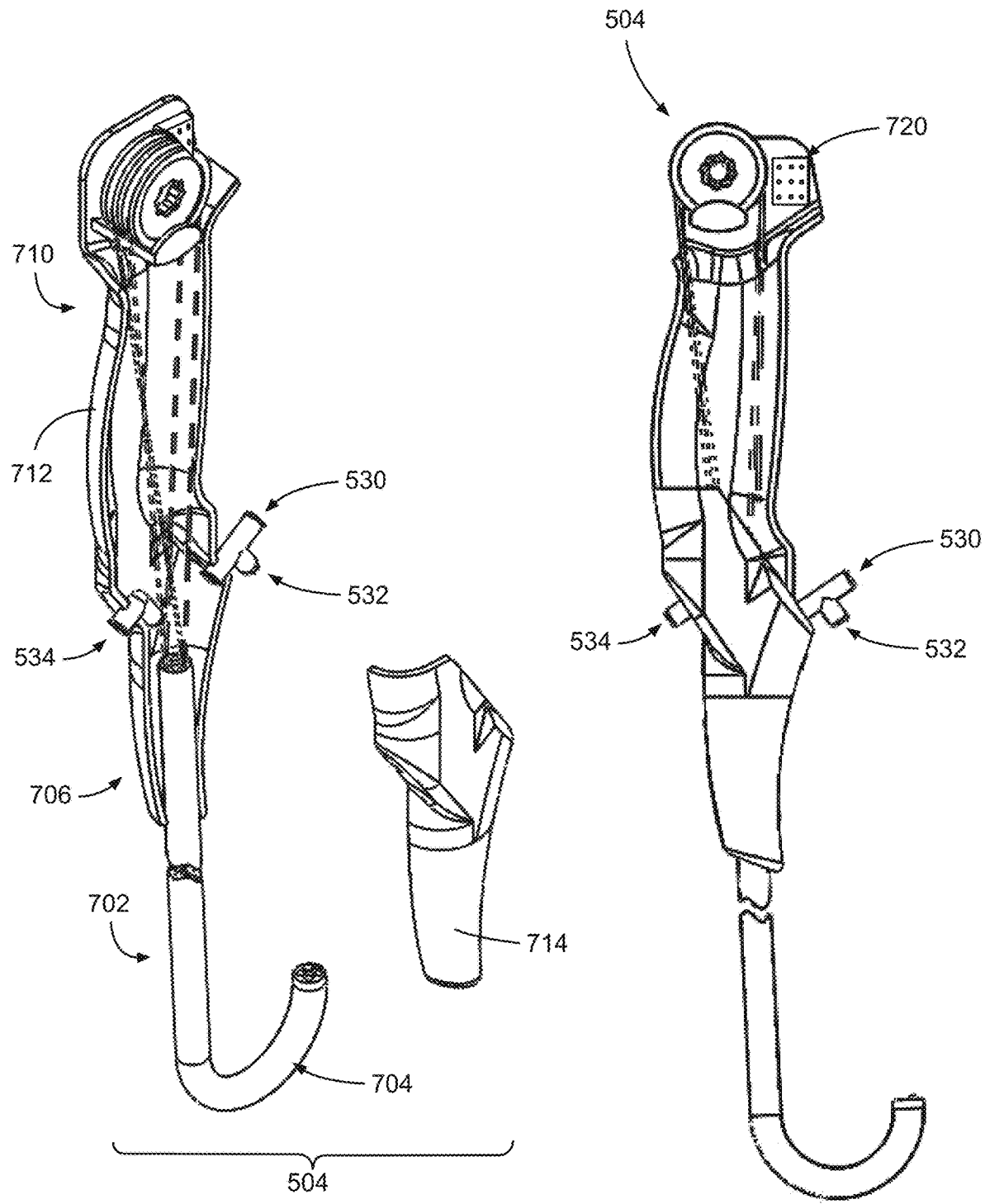
FIG. 18A depicts a front, partially exploded isometric view of the disposable shaft assembly of FIG. 10.
FIG. 18B depicts a front view of the disposable shaft assembly.
Figure 19:
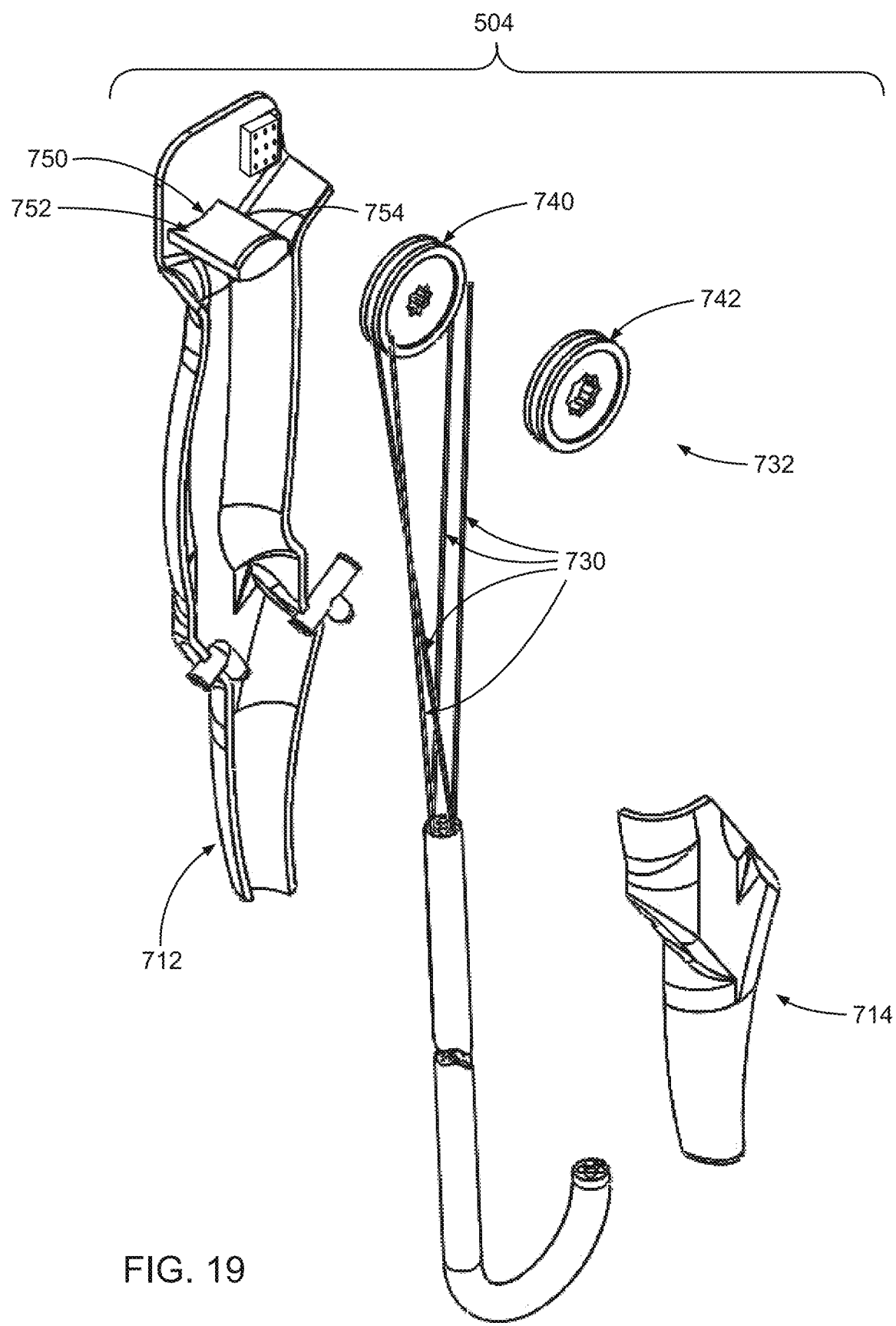
FIG. 19 depicts front, exploded, isometric view of the disposable shaft assembly.

FIGS. 18A-19 illustrate the disposable shaft assembly. The disposable shaft assembly includes a shaft 702 having an articulating distal portion 704 and a proximal portion 706 connected to a housing 710. The housing can have a first portion 712 and a second portion 714 that sandwich the proximal portion of the shaft.

An optical and/or electrical connector 720 arranged to communicate with the optical and/or electrical connector of the controller of the reusable hand-piece can be mounted to the housing of the disposable shaft assembly. The optical and/or electrical connector of the disposable shaft assembly is arranged to receive light and/or electricity from the controller.

The disposable shaft assembly includes one or more articulation wires 730 associated with an articulation wire articulating assembly, such as a cam assembly 732. The cam assembly can include a first cam 740 and a second cam 742 arranged to actuate the one or more articulation wires in response to rotation of the actuation control of the reusable hand-piece.

The disposable shaft assembly includes a cam assembly support. The cam assembly support can include a shelf 750 of the disposable shaft assembly. The shelf, alone or in cooperation with another feature such as the articulation wires, is arranged to retain the cam assembly against the disposable shaft assembly when the disposable shaft assembly is not connected to the reusable hand-piece. For example, the shelf can extend between the cam assembly and the proximal portion of the shaft so that the tension of the articulation wires pulls the cam assembly against the shelf.

The shelf can define a recess 752 arranged to receive the cam assembly. The recess can be defined by a concave surface matching a curvature of the cam assembly so as to retain the cam assembly on the shelf. Additionally or alternatively, the shelf may include an end wall 754 arranged to resist the cam assembly from moving (e.g., sliding) from the shelf.

FIGS. 20A and 20B illustrate an alternative to the cam assemblies described above. In this alternative arrangement, a rack and pinion assembly 800 includes a first gear rack 802 and a second gear rack 804 that each engage a first gear 808, and a third gear rack 812 and fourth gear rack 814 that each engage a second gear 818. When the reusable hand-piece is attached to the disposable shaft assembly, the first gear engages the cam engaging portion of the first drive shaft and the second gear engages the cam engaging portion of the second drive shaft. Accordingly, the first gear rotates when an operator rotates the first articulation control knob, and the second gear rotates when an operator rotates the second articulation control knob.

Articulation wires 830 are attached to the gear racks. Upon rotation of the first gear and/or second gear, the associated gear racks translate which, in turn, actuates the associated articulation wires. For example, upon rotation of the first gear, one of the first and second gear racks translates upwards so as to pull the associated articulation wire and the other gear rack translates downwards.

Figure 21:
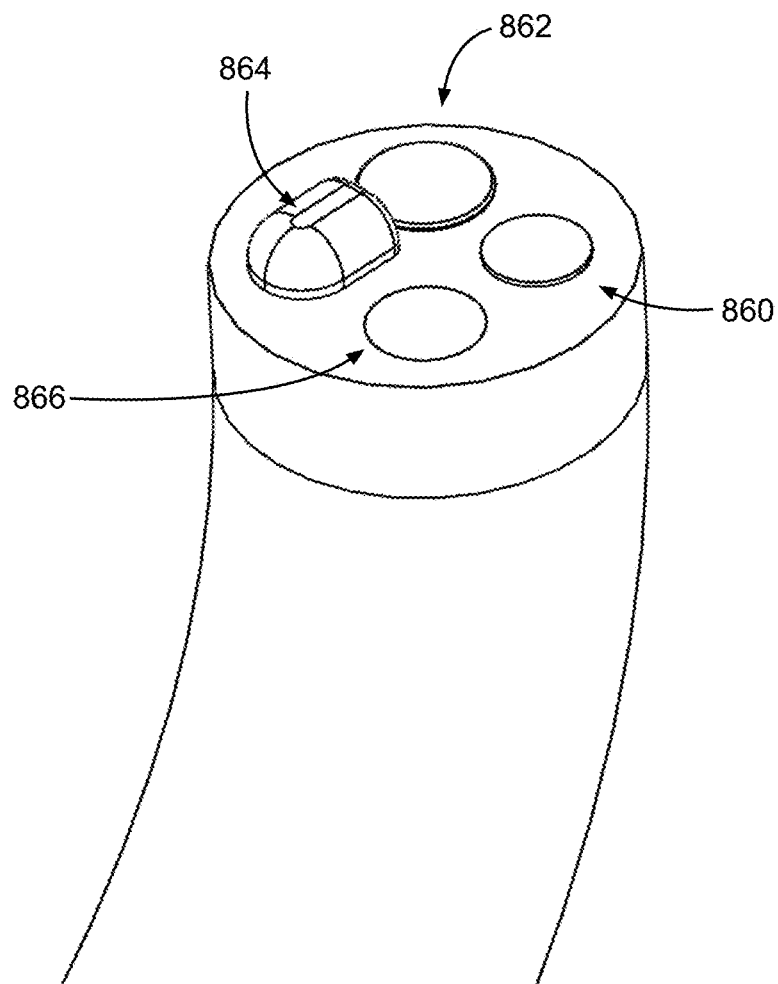
FIG. 21 depicts the distal end of the disposable shaft assembly of FIG. 10.

FIG. 21 illustrates the distal end of the articulating distal portion of the shaft. The distal end can include a light emitter 860, an imaging device 862, a first opening 864 to an irrigation or aspiration lumen of the shaft, and a second opening 866 to a lumen of the shaft, such as one that is arranged to receive a tool (e.g., forceps, a cutter, and/or a ligation device).

Figure 22:
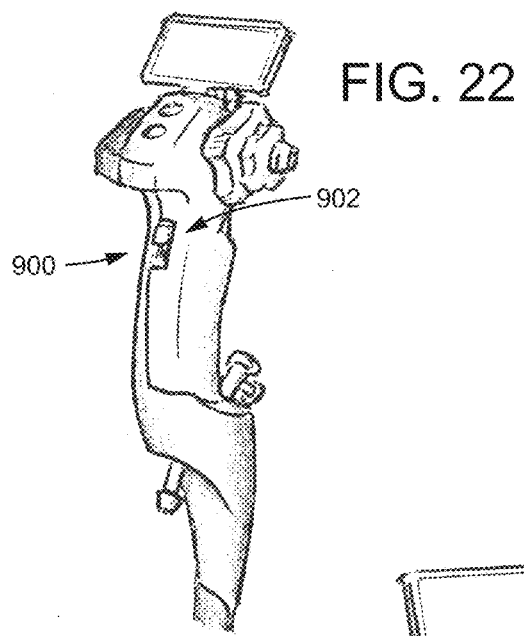
FIG. 22 depicts a perspective view of an endoscope assembly having a latch.
Figure 23:
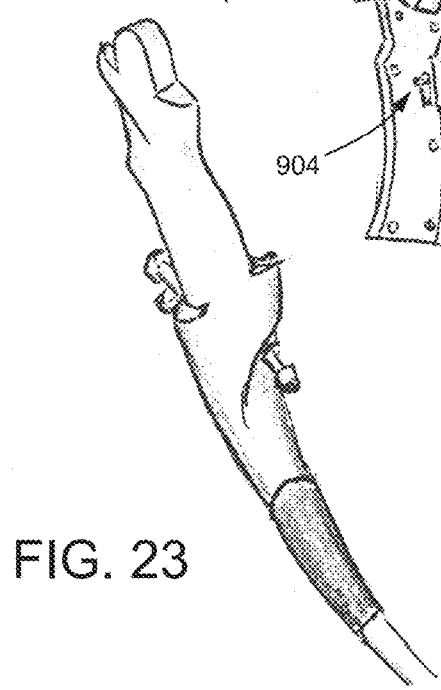
FIG. 23 depicts a perspective view of the endoscope assembly of FIG. 22 with the reusable hand-piece detached from the disposable shaft assembly.
Figure 24:
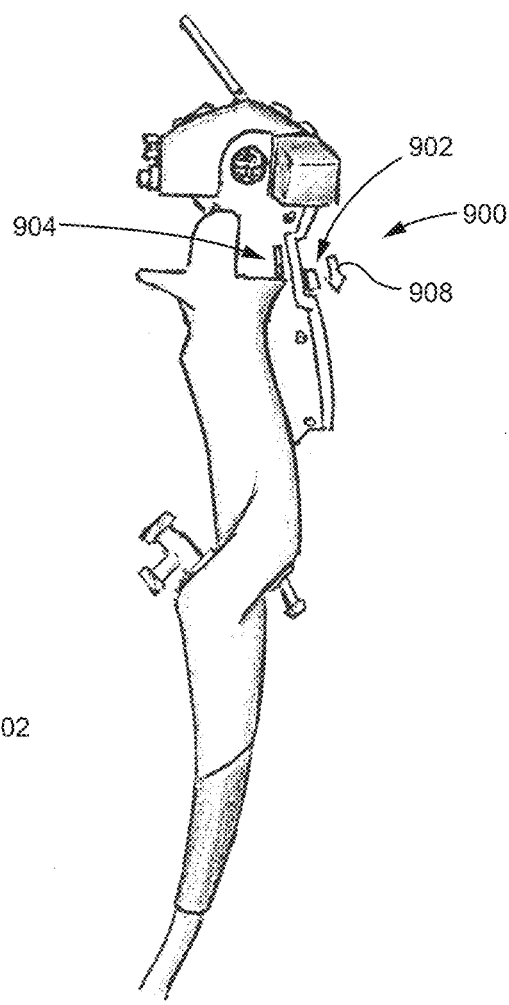
FIG. 24 depicts a rear view of the endoscope assembly of FIG. 22 with the reusable hand-piece detached from the disposable shaft assembly and the latch actuated.

FIGS. 22-24 illustrate a coupler for securing the reusable hand-piece to the disposable shaft assembly. As shown in FIG. 22, the coupler 900 can comprise an external portion 902 and an internal portion 904. When the reusable hand-piece is attached to the disposable shaft assembly, the external portion (e.g., a button, slider, and/or switch) is actuatable by a user's hand and the internal portion is positioned inside the endoscope assembly.

To disconnect the reusable hand-piece from the disposable shaft assembly, a user presses the external portion of the coupler so as to move the internal portion, as shown by arrow 908 in FIG. 24. Actuating the external portion of the coupler disengages the internal portion of the coupler from a surface of disposable shaft assembly so as to allow the reusable hand-piece to be separated from the disposable shaft assembly.

FIGS. 25 and 26 illustrate another coupler embodiment. In this embodiment, the coupler comprises a lever 920 that is pivotable from a locked configuration to an unlocked configuration and vice-versa.

Figures 27, 28:
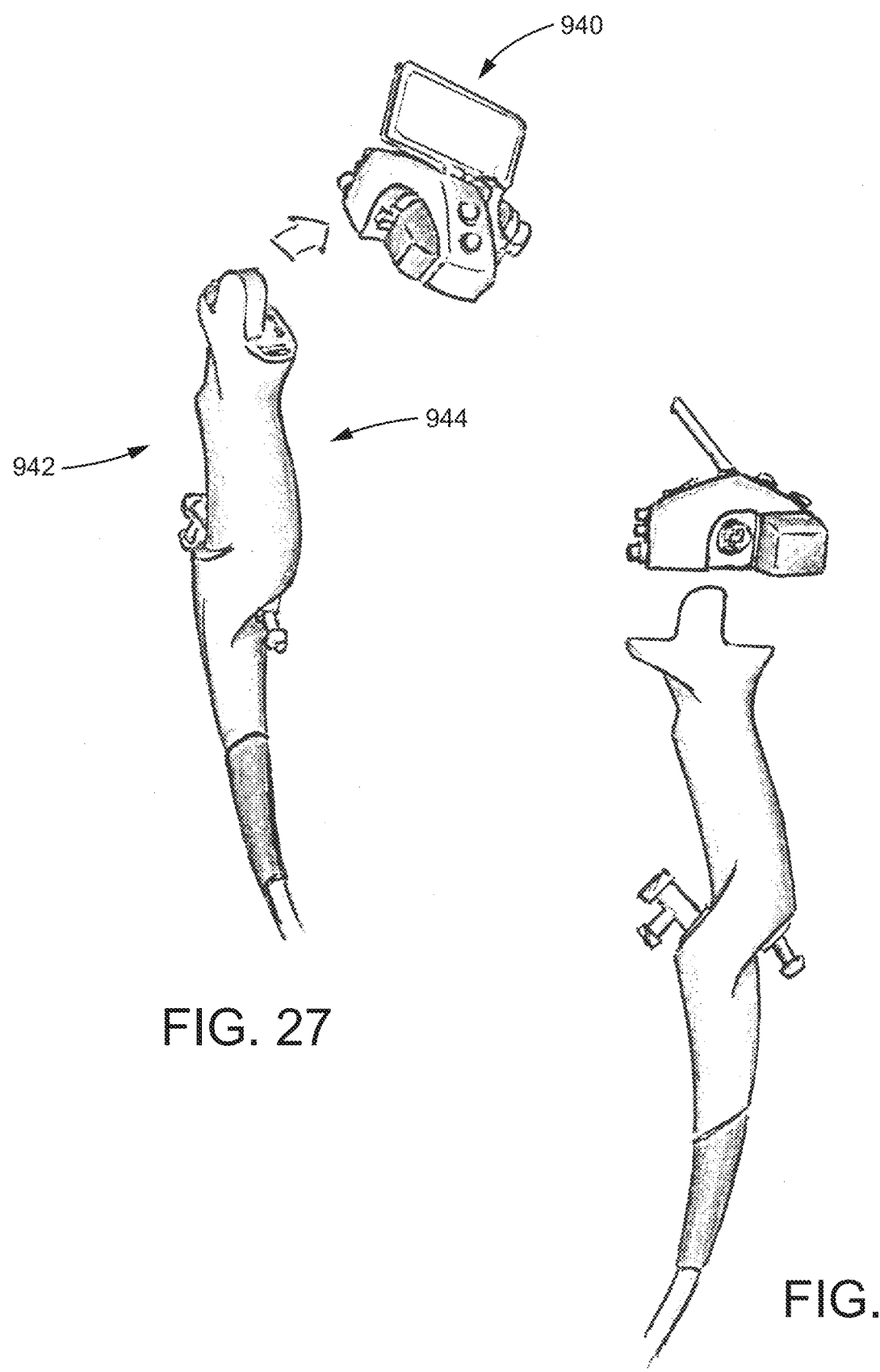
FIG. 27 depicts a perspective view of an endoscope assembly with the reusable hand-piece detached from the disposable shaft assembly.
FIG. 28 depicts a rear view of the endoscope assembly of FIG. 27 with the reusable hand-piece detached from the disposable shaft assembly.

FIGS. 27 and 28 illustrate another arrangement of an endoscope assembly comprising a reusable hand-piece 940 and a disposable shaft assembly 942. In this embodiment, the handle 944 of the endoscope is defined entirely by one of the separable portions (i.e., the reusable hand-piece or the disposable shaft assembly). In earlier illustrated embodiments, the handle is defined by portions of both the reusable hand-piece and the disposable shaft assembly.

Turning to FIGS. 29A and 29B, the endoscope system may comprise a second disposable shaft assembly 107. The second disposable shaft assembly 107 has an articulation wire actuating assembly mounted to a housing of the second disposable shaft assembly, the articulation wire actuating assembly attached to an articulation wire extending along a length of the second disposable shaft assembly. The housing of the reusable hand-piece assembly is removably connectable to the housing of the second disposable shaft assembly. The articulation control engages the articulation wire actuating assembly of the second disposable shaft assembly when the housing of the reusable hand-piece assembly is connected to the housing of the second disposable shaft assembly.

The term "removably coupled" as used herein, regardless of tense, means capable of being separated without destructive means (e.g., saw, hammer, blow torch, etc.).

The following numbered clauses set out specific embodiments that may be useful in understanding the present invention:

1. An endoscope, comprising:
a reusable hand-piece and a disposable shaft assembly, wherein the means for articulation is transferred from the reusable hand-piece to the disposable shaft assembly by means of concentric drive shafts.

2. The endoscope of clause 1, wherein the concentric drive shafts transmit torque to the articulation pulleys by means of oval, spline, square, or star geometric features.

3. The endoscope of clause 1 or 2, wherein the reusable hand-piece incorporates a battery, a control board, and means for wirelessly transmitting image data to an external storage device.

4. An endoscope, comprising:
a reusable hand-piece assembly and a first disposable shaft assembly;
an articulation control mounted to a housing of the reusable hand-piece assembly; and
an articulation wire actuating assembly mounted to a housing of the first disposable shaft assembly, the articulation wire actuating assembly attached to an articulation wire extending along a length of the first disposable shaft assembly;
wherein the housing of the reusable hand-piece assembly is removably connected to the housing of the first disposable shaft assembly; and
wherein the articulation control engages the articulation wire actuating assembly when the housing of the reusable hand-piece assembly is connected to the housing of the first disposable shaft assembly.

5. The endoscope of clause 4, wherein the housing of the reusable hand-piece assembly is arranged for connection to and disconnection from the housing of the first disposable shaft assembly without hand tools.

6. The endoscope of clause 4 or 5, wherein the housing of the reusable hand-piece assembly is removably connected to the housing of the first disposable shaft assembly by one or more latches.

7. The endoscope of any one of clauses 4-6, wherein the housing of the reusable hand-piece assembly is removably connected to the housing of the first disposable shaft assembly by one or more magnets.

8. The endoscope of any one of clauses 4-7, wherein the reusable hand-piece assembly is absent a fluid connector that communicates with a lumen of the first disposable shaft assembly.

9. The endoscope of any one of clauses 4-8, wherein the housing of the first disposable shaft assembly includes a port in fluid communication with a lumen of a shaft of the first disposable shaft assembly.

10. The endoscope of any one of clauses 4-9, wherein the articulation control of reusable hand-piece includes a first articulation control knob and a second articulation control knob.

11. The endoscope of clause 10, wherein the first articulation control knob has a first drive shaft and the second articulation control knob has a second drive shaft, and wherein the first and second drive shafts are concentric.

12. The endoscope of any one of clauses 4-11, wherein:
an electronics module is mounted to the housing of the reusable hand-piece assembly.

13. The endoscope of clause 12, wherein:
the electronics module has a connector that engages a connector of the first disposable shaft assembly when the housing of the reusable hand-piece assembly is connected to the housing of the first disposable shaft assembly.

14. A method, comprising:
connecting a housing of a reusable hand-piece to a housing of a first disposable shaft assembly, wherein said reusable hand-piece has articulation controls and an electronics module and said first disposable shaft assembly has an articulation wire actuating assembly and a connector; and
wherein said connecting connects the articulation controls to the articulation wire actuating assembly and the electronics module to the connector of the first disposable shaft assembly.

15. The method of clause 14, comprising:
separating the housing of the reusable hand-piece from the housing of the first disposable shaft assembly so as to separate the articulation controls from the articulation wire actuating assembly and the electronics module from the connector of the first disposable shaft assembly.

16. The method of clause 14 or 15, comprising:
connecting the housing of the reusable hand-piece to a housing of a second disposable shaft assembly, wherein said second disposable shaft assembly has an articulation wire actuating assembly and a connector; and
wherein said connecting connects the articulation controls to the articulation wire actuating assembly and the electronics module to the connector of the second disposable shaft assembly.

17. An endoscope system, comprising:
the endoscope of any one of clauses 4-13 and a second disposable shaft assembly;
wherein the second disposable shaft assembly has an articulation wire actuating assembly mounted to a housing of the second disposable shaft assembly, the articulation wire actuating assembly attached to an articulation wire extending along a length of the second disposable shaft assembly;
wherein the housing of the reusable hand-piece assembly is removably connectable to the housing of the second disposable shaft assembly; and
wherein the articulation control engages the articulation wire actuating assembly of the second disposable shaft assembly when the housing of the reusable hand-piece assembly is connected to the housing of the second disposable shaft assembly.

18. The system of clause 17, wherein the first disposable shaft assembly differs from the second disposable shaft assembly in at least one of shaft length and shaft diameter.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An endoscope, comprising:
a reusable hand-piece and a first disposable shaft assembly, the first disposable shaft assembly defining a longitudinal axis, wherein the reusable hand-piece articulates the first disposable shaft assembly by means of concentric drive shafts;
an electronics module is mounted to a housing of the reusable hand-piece assembly; and
wherein the electronics module has a connector that engages a connector of the first disposable shaft assembly when the housing of the reusable hand-piece assembly is connected to a housing of the first disposable shaft assembly, and wherein the connector of the electronics module engages the connector of the first disposable shaft assembly along a direction transverse to the longitudinal axis.

2. The endoscope of claim 1, wherein the concentric drive shafts transmit torque to articulation pulleys by oval, spline, square, or star geometric features.

3. The endoscope of claim 1, wherein the reusable hand-piece incorporates a battery, a control board, and means for wirelessly transmitting image data to an external storage device.

4. An endoscope, comprising:
a reusable hand-piece assembly and a first disposable shaft assembly;
an articulation control mounted to a housing of the reusable hand-piece assembly;
an articulation wire actuating assembly mounted to a housing of the first disposable shaft assembly, the articulation wire actuating assembly attached to an articulation wire extending along a first direction and along a length of the first disposable shaft assembly; and
an electronics module mounted to the housing of the reusable hand-piece assembly;
wherein the housing of the reusable hand-piece assembly is removably connected to the housing of the first disposable shaft assembly along a second direction;
wherein the articulation control engages the articulation wire actuating assembly when the housing of the reusable hand-piece assembly is connected to the housing of the first disposable shaft assembly;
wherein articulation control of the reusable hand-piece includes a first articulation control knob and a second articulation control knob;
wherein the first articulation control knob has a first drive shaft and the second articulation control knob has a second drive shaft, and wherein the first and second drive shafts are concentric and extend along the second direction;
wherein the electronics module has a connector that engages a connector of the first disposable shaft assembly when the housing of the reusable hand-piece assembly is connected to the housing of the first disposable shaft assembly along the second direction; and
wherein the first direction is transverse to the second direction.

5. The endoscope of claim 4, wherein the housing of the reusable hand-piece assembly is arranged for connection to and disconnection from the housing of the first disposable shaft assembly without hand tools.

6. The endoscope of claim 4, wherein the housing of the reusable hand-piece assembly is removably connected to the housing of the first disposable shaft assembly by one or more latches.

7. The endoscope of claim 4, wherein the housing of the reusable hand-piece assembly is removably connected to the housing of the first disposable shaft assembly by one or more magnets.

8. The endoscope of claim 4, wherein the reusable hand-piece assembly is absent a fluid connector that communicates with a lumen of the first disposable shaft assembly.

9. The endoscope of claim 4, wherein the housing of the first disposable shaft assembly includes a port in fluid communication with a lumen of a shaft of the first disposable shaft assembly.

10. An endoscope system, comprising:
the endoscope of claim 4 and a second disposable shaft assembly;
wherein the second disposable shaft assembly has an articulation wire actuating assembly mounted to a housing of the second disposable shaft assembly, the articulation wire actuating assembly attached to an articulation wire extending along a length of the second disposable shaft assembly;
wherein the housing of the reusable hand-piece assembly is removably connectable to the housing of the second disposable shaft assembly; and
wherein the articulation control engages the articulation wire actuating assembly of the second disposable shaft assembly when the housing of the reusable hand-piece assembly is connected to the housing of the second disposable shaft assembly.

11. The system of claim 10, wherein the first disposable shaft assembly differs from the second disposable shaft assembly in at least one of shaft length and shaft diameter.

12. The endoscope of claim 4, wherein the articulation wire actuating assembly comprises a rack and pinion assembly;
wherein the rack and pinion assembly includes a first gear rack coupled to the first articulation control knob through a first gear and a second gear rack coupled to the second articulation control knob through a second gear;

wherein the articulation wire extending along a length of the first disposable shaft assembly is a first articulation wire coupled to the first gear rack such that rotation of the first articulation control knob translates the first gear rack; and wherein a second articulation wire is coupled to the second gear rack such that rotation of the second articulation control knob translates the second gear rack.

13. The endoscope of claim 12, comprising: a third gear rack associated with the first articulation control knob and a fourth gear rack associated with the second articulation control knob;

wherein rotation of the first articulation control knob translates the third gear rack in a direction opposite that of the first gear rack; and wherein rotation of the second articulation control knob translates the fourth gear rack in a direction opposite that of the second gear rack.

* * * * *